United States Patent
Nakamura et al.

(10) Patent No.: US 10,946,028 B2
(45) Date of Patent: Mar. 16, 2021

(54) POLYMER CONJUGATE OF SULFOXIDE DERIVATIVE-COORDINATED PLATINUM(II) COMPLEX

(71) Applicant: Nippon Kayaku Kabushiki Kaisha, Tokyo (JP)

(72) Inventors: Masaharu Nakamura, Tokyo (JP); Tsuyoshi Fukuda, Tokyo (JP); Ken Yamakawa, Tokyo (JP); Takuya Kato, Tokyo (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 16/062,212

(22) PCT Filed: Dec. 16, 2016

(86) PCT No.: PCT/JP2016/087521
§ 371 (c)(1),
(2) Date: Jun. 14, 2018

(87) PCT Pub. No.: WO2017/110669
PCT Pub. Date: Jun. 29, 2017

(65) Prior Publication Data
US 2018/0369254 A1 Dec. 27, 2018

(30) Foreign Application Priority Data
Dec. 22, 2015 (JP) .............................. JP2015-250255

(51) Int. Cl.
| | |
|---|---|
| *A61K 31/282* | (2006.01) |
| *A61K 31/555* | (2006.01) |
| *A61K 47/54* | (2017.01) |
| *A61K 47/60* | (2017.01) |
| *A61K 47/62* | (2017.01) |
| *A61K 47/64* | (2017.01) |
| *A61P 35/00* | (2006.01) |
| *C08G 65/334* | (2006.01) |
| *C08G 69/08* | (2006.01) |
| *C08G 69/48* | (2006.01) |
| *C08G 81/00* | (2006.01) |
| *C08L 71/02* | (2006.01) |

(52) U.S. Cl.
CPC .......... *A61K 31/555* (2013.01); *A61K 31/282* (2013.01); *A61K 47/541* (2017.08); *A61K 47/60* (2017.08); *A61K 47/62* (2017.08); *A61K 47/645* (2017.08); *A61P 35/00* (2018.01); *C08G 65/3344* (2013.01); *C08G 69/08* (2013.01); *C08G 69/48* (2013.01); *C08G 81/00* (2013.01); *C08L 71/02* (2013.01); *C08G 2261/126* (2013.01)

(58) Field of Classification Search
CPC .. C08G 69/08; C08G 65/3344; A61K 31/282; A61K 47/645; A61P 35/00
See application file for complete search history.

(56) References Cited

U.S. PATENT DOCUMENTS

| | | |
|---|---|---|
| 5,107,007 A | 4/1992 | Farrell |
| 5,624,919 A | 4/1997 | Farrell |
| 6,350,740 B1 | 2/2002 | Farrell |
| 7,125,546 B2 | 10/2006 | Kataoka et al. |
| 2004/0161403 A1 | 8/2004 | Zhao et al. |
| 2006/0067910 A1 | 3/2006 | Kitagawa et al. |
| 2006/0222696 A1 | 10/2006 | Okada et al. |
| 2007/0148125 A1 | 6/2007 | Kataoka et al. |
| 2008/0113028 A1 | 5/2008 | Shimizu et al. |
| 2008/0249256 A1 | 10/2008 | Kobayashi et al. |
| 2009/0162313 A1 | 6/2009 | Kitagawa et al. |
| 2011/0081404 A1 | 4/2011 | Okada et al. |
| 2011/0110881 A1 | 5/2011 | Kataoka et al. |
| 2012/0116051 A1 | 5/2012 | Kitagawa et al. |
| 2014/0288244 A1* | 9/2014 | Yamamoto .......... C08G 65/333 525/434 |

(Continued)

FOREIGN PATENT DOCUMENTS

| | | |
|---|---|---|
| CN | 103450281 A | 12/2013 |
| CN | 103874722 A | 6/2014 |
| GB | 2304712 A | 3/1997 |

(Continued)

OTHER PUBLICATIONS

Kataoka et al. "Anticancer drug comprising cyclic rgd sequence-containing peptide" WO 2014084378 A1 (Jun. 5, 2014) English Machine Translation (obtained from Google Patents). (Year: 2014).*
European communication dated Jun. 27, 2019 in corresponding European patent application No. 16878558.2.
Cabral et al., "Preparation and Biological Properties of dichloro(1,2-diaminocyclohexane)platinum(II) (DACHPt)-loaded polymeric micelles", Journal of Controlled Release, vol. 101, pp. 223-232, 2005.

(Continued)

*Primary Examiner* — Amanda L. Aguirre

(74) *Attorney, Agent, or Firm* — Nields, Lemack & Frame, LLC

(57) ABSTRACT

A DDS preparation of a platinum complex, which exhibits a superior antitumor effect required as a medicine and reduced side effects, that is, a clinically usable DDS preparation of a platinum complex, which is conjugated to a polymer carrier that is different from conventional carriers, is desired.

Provided is a polymer conjugate of a platinum(II) complex, the polymer conjugate including: a block copolymer having a polyethylene glycol structural moiety and a polyaspartic acid moiety or a polyglutamic acid moiety; a sulfoxide derivative introduced into a side-chain carboxyl group of the block copolymer; and a platinum(II) complex coordinate-bonded to a sulfoxide group of the sulfoxide derivative.

5 Claims, No Drawings

(56) References Cited

U.S. PATENT DOCUMENTS

| | | | |
|---|---|---|---|
| 2014/0328919 A1* | 11/2014 | Zhang | A61K 47/40 424/489 |
| 2014/0363491 A1 | 12/2014 | Okada et al. | |

FOREIGN PATENT DOCUMENTS

| | | | | |
|---|---|---|---|---|
| JP | 5-500218 A | 1/1993 | | |
| JP | 5-117385 A | 5/1993 | | |
| JP | 7-69900 A | 3/1995 | | |
| JP | 9-504275 A | 4/1997 | | |
| JP | 3268913 B2 | 3/2002 | | |
| JP | 2006-512462 A | 4/2006 | | |
| JP | 3955992 B2 | 8/2007 | | |
| JP | 2008-538105 A | 10/2008 | | |
| JP | 2011-105792 A | 6/2011 | | |
| JP | 4745664 B2 | 8/2011 | | |
| JP | 2011-173908 A | 9/2011 | | |
| JP | 5458255 B2 | 4/2014 | | |
| RU | 2335512 C2 | 10/2008 | | |
| RU | 2382056 C2 | 2/2010 | | |
| RU | 2447095 C2 | 4/2012 | | |
| WO | 89/09598 A1 | 10/1989 | | |
| WO | WO-8909598 A1 * | 10/1989 | | C07F 15/0093 |
| WO | 2005/056641 A1 | 6/2005 | | |
| WO | 2010/131675 A1 | 11/2010 | | |
| WO | 2011/058776 A1 | 5/2011 | | |
| WO | 2014/084378 A1 | 6/2014 | | |
| WO | WO-2014084378 A1 * | 6/2014 | | C07K 14/755 |

OTHER PUBLICATIONS

Cabral et al., "Optimization of (1,2-diamino-cyclohexane)platinum(II)-loaded polymeric micelles directed to improved tumor targeting and enhanced antitumor activity", Journal of Controlled Release, vol. 121, pp. 146-155, 2007.

Fischer et al., "Cisplatin and dimethyl sulfoxide react to form an adducted compound with reduced cytotxicity and neurotoxicity", NeuroToxicology, vol. 29, pp. 444-452, 2008.

Hall et al., "Say No to DMSO: Dimethylsulfoxide Inactivates Cisplatin, Carboplatin, and Other Platinum Complexes", Journal of Cancer Research, vol. 74, No. 14, pp. 3913-3922, 2014.

Nishiyama et al., "Preparation and Characterization of Self-Assembled Polymer-Metal Complex Micelle from cis-Dichlorodiammineplatinum(II) and Poly(ethylene glycol)-Poly(α,β-aspartic acid) Block Copolymer in an Aqueous Medium", Langmuir, vol. 15, pp. 377-383, 1999.

Nishiyama et al., "Cisplatin-Loaded Polymer-Metal Complex Micelle with Time-Modulated Decaying Property as a Novel Drug Delivery System", Pharmaceutical Research, vol. 18, No. 7, pp. 1035-1041, 2001.

Nishiyama et al., "Novel Cisplatin-Incorporated Polymeric Micelles Can Eradicate Solid Tumors in Mice", Cancer Research, vol. 63, pp. 8977-8983, 2003.

Rafi et al., "Polymeric Micelles Incorporating (1,2 diaminocyclohexane)platinum (II) Suppress the Growth of Orthotopic Scirrhous Gastric Tumors and their Lymph Node Metastasis", Journal of Controlled Release, vol. 159, pp. 189-196, 2012.

Yang et al., "Biodegradable Polymer-Platinum Drug Conjugates to Overcome Platinum Drug Resistance", RSC Advances, vol. 5, pp. 83343-83349, 2015.

Yokoyama et al., "Introduction of Cisplatin into Polymeric Micelle", Journal of Controlled Release, vol. 39, pp. 351-356, 1996.

International Search Report and Written Opinion dated Mar. 21, 2017 in corresponding PCT application No. PCT/JP2016/087521.

Bahrami et al., "TMSCl-Promoted Selective Oxidation of Sulfides to Sulfoxides with Hydrogen Peroxide", Tetrahedron Letters, vol. 51, pp. 6939-6941, 2010.

Farrell et al., "Chemical Properties and Antitumor Activity of Complexes of Platinum Containing Substituted Sulfoxides [PtCl(R'R"SO)(diamine)]NO3 Chirality and Leaving-Group Ability of Sulfoxide Affecting Biological Activity", Inorganic Chemistry, vol. 29, No. 3, pp. 397-403, 1990.

Fontes et al., "Synthesis, Characterization, and Reactivity of trans-[PtCl(R'R"SO)(A)2]NO3 (R'R"SO=Me2SO, MeBzSO, MePhSO; A=NH3, py, pic). Crystal Structure of trans-[PtCl(Me2SO)(py)2]+", Inorganic Chemistry, vol. 40, No. 8, pp. 1745-1750, 2001.

Johnstone et al., "The Chiral Potential of Phenanthriplatin and its Influence on Guanine Binding", Journal of the American Chemical Society, vol. 136, pp. 2126-2134, 2014.

Ternay Jr et al., "The Borohydride Reduction of Thioxanthone Sulfoxide. A Base-Induced Dehydration of Thioxanthenol Sulfoxide", Journal of Organic Chemistry, vol. 32, pp. 3814-3817, 1967.

Wang et al., "Injectable Biodegradable Hydrogels with Tunable Mechanical Properties for the Stimulation of Neurogenesic Differentiation of Human Mesenchymal Stem Cells in 3D Culture", Biomaterials, vol. 31, pp. 1148-1157, 2010.

Wilson et al., "Synthetic Methods for the Preparation of Platinum Anticancer Complexes", Chemical Reviews, vol. 114, pp. 4470-4495, 2014.

Yu et al., "Anticancer Activity of a Series of Platinum Complexes Integrating Demethylcantharidin with Isomers of 1,2-diaminocyclohexane", Bioorganic & Medicinal Chemistry Letters, vol. 16, pp. 1686-1691, 2006.

Yuste et al., "Methyl Sulfinates as Electrophiles in Friedel-Crafts Reactions. Synthesis of Aryl Sulfoxides", The Journal of Organic Chemistry, vol. 76, pp. 4635-4644, 2011.

Russian communication, with English translation, dated Apr. 15, 2019 in corresponding Russian patent application No. 2018121344/04.

Chin et al., "Tuning the Activity of Platinum(IV) Anticancer Complexes through Asymmetric Acylation", Journal of Medicinal Chemistry, vol. 55, pp. 7571-7582, 2012.

Taiwanese communication, with English translation, dated May 5, 2020 in corresponding Taiwanese patent application No. 105142561.

Chinese communication, with English translation, dated Mar. 31, 2020 in corresponding Chinese patent application No. 201680075647.8.

Australian communication dated Jun. 15, 2020 in corresponding Australian patent application No. 2016374759.

Japanese communication, with English translation, dated Jun. 30, 2020 in corresponding Japanese patent application No. 2017-558083.

* cited by examiner

POLYMER CONJUGATE OF SULFOXIDE DERIVATIVE-COORDINATED PLATINUM(II) COMPLEX

TECHNICAL FIELD

The present invention relates to a polymer conjugate of a platinum(II) complex having antitumor activity, to which a polymeric sulfoxide derivative is coordinate-bonded, and a medicine comprising the polymer conjugate as an active ingredient.

RELATED ART

Platinum complexes such as cisplatin and oxaliplatin are known to exhibit an antitumor effect by inhibiting DNA replication and inducing apoptosis, and thus, platinum complexes are clinically used as a key drug for combination therapy in various cancer areas. However, the platinum complexes are known to cause renal disorders, nausea and vomiting, peripheral nerve disorders, and bone marrow suppression as side effects, and these side effects pose problems in clinical use of the platinum complexes.

For the purpose of reducing these side effects and enhancing therapeutic effects, the development of platinum complexes that utilize drug delivery technologies using polymers is underway. Examples of DDS (drug delivery system) preparations of platinum complexes that have hitherto advanced to the clinical trial stage include a coordination compound of diaminocyclohexaneplatinum(II) and a block copolymer (NC-4016; see Patent Literature 1), targeted liposomes encapsulating oxaliplatin (MBP-426; see Patent Literature 2), and a coordination compound of cisplatin and a block copolymer (see Patent Literature 3).

On the other hand, research on low molecular weight platinum complexes is also in progress, and regarding tetracoordinated platinum(II) complexes such as cisplatin and oxaliplatin, complexes having, as their ligands, a sulfoxide derivative, a N-heterocycle derivative, and a thiourea derivative, and the like have been reported (see Non-Patent Literature 1).

Regarding a tetracoordinated platinum(II) complex having a sulfoxide derivative as a ligand, complexes having dimethyl sulfoxide, methyl phenyl sulfoxide, diphenyl sulfoxide, and the like as sulfoxide derivatives have been reported, and it was confirmed that these complexes exhibit an antitumor effect in animal models (see Non-Patent Literature 2). Furthermore, a tetracoordinated platinum(II) complex having a sulfoxide derivative as a ligand and having two amine ligands in trans configuration is also known (see Non-Patent Literature 3).

However, there has been no report to hitherto on a DDS preparation of a platinum complex to which a polymeric sulfoxide derivative is coordinate-bonded, and no DDS preparations of a platinum complex, including the compounds described in Patent Literatures 1 to 3 mentioned above, have yet been brought to the market.

PRIOR ART DOCUMENTS

Patent Literature

Patent Literature 1: JP 3955992 B2
Patent Literature 2: JP 2008-538105 A
Patent Literature 3: JP 5458255 B2

Non Patent Literature

Non Patent Literature 1: Chemical Reviews, 2014, 114, 4470-4495
Non Patent Literature 2: Inorganic Chemistry, 1990, 29, 397-403
Non Patent Literature 3: Inorganic Chemistry, 2001, 40, 1745-1750

SUMMARY OF INVENTION

Problem to be Solved

A DDS preparation of a platinum complex exhibiting a high antitumor effect that is required as a medicine is still unavailable, and a DDS preparation of a platinum complex that is clinically usable, the platinum complex being conjugated to a polymer carrier different from those used in the DDS preparations mentioned above, is desired. That is, it is expected that a DDS preparation of a platinum complex will exhibit a high antitumor effect and the like, which is obtained by coordinate-bonding platinum to a polymeric sulfoxide derivative and thereby enhancing the capability for cellular uptake of the platinum complex.

Means to Solve the Problem

The inventors of the present invention conducted a thorough research in order to solve the problems described above, and as a result, the inventors found that a DDS preparation of a platinum complex obtainable by introducing a sulfoxide derivative into a side-chain carboxyl group in a block copolymer having a polyethylene glycol structural moiety and a polyaspartic acid moiety or a polyglutamic acid moiety, and coordinate-bonding the sulfoxide group to platinum, exhibits superior performance. Thus, the inventors completed the present invention.

That is, the present invention relates to the following items (1) to (12).
(1) A polymer conjugate of a platinum(II) complex, the polymer conjugate comprising:
 a block copolymer having a polyethylene glycol structural moiety and a polyaspartic acid moiety or a polyglutamic acid moiety;
 a sulfoxide derivative introduced into a side-chain carboxyl group of the block copolymer; and
 a platinum(II) complex coordinate-bonded to a sulfoxide group of the sulfoxide derivative.
(2) The polymer conjugate of a platinum(II) complex according to (1), wherein the polymer conjugate is represented by the following General Formula (I):

[Chemical Formula 1]

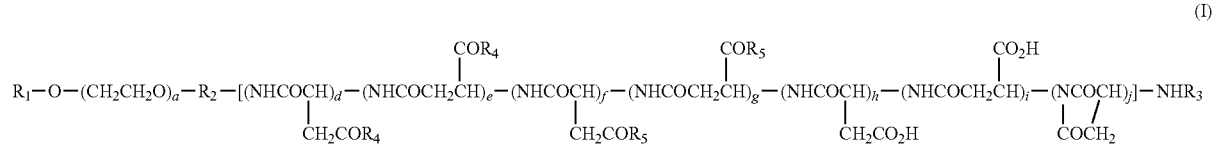

(I)

wherein $R_1$ represents a hydrogen atom, a (C1-C10) alkyl group optionally having a substituent, or a (C6-C10) aryl group optionally having a substituent; $R_2$ represents a bonding group; $R_3$ represents a hydrogen atom or a (C1-C6) acyl group; $R_4$ represents a substituent represented by the following General Formula (II):

[Chemical Formula 2]

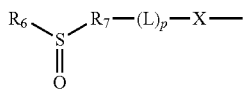
(II)

[wherein X represents an oxygen atom or $NR_8$; $R_8$ represents a hydrogen atom, a (C1-C10) alkyl group, or a (C6-C10) aryl group optionally having a substituent; L represents a linker; p represents 0 or 1; $R_6$ represents a (C1-C10) alkyl group optionally having a substituent, a (C6-C10) aryl group optionally having a substituent, or a (C7-C15) aralkyl group optionally having a substituent; and $R_7$ represents a residue obtained by eliminating H from the substituent representing $R_6$, or a cyclic structure formed by $R_6$ and $R_7$ bonded together], or the following General Formula (III):

[Chemical Formula 3]

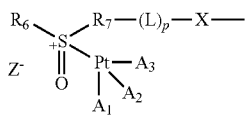
(III)

[wherein X represents an oxygen atom or $NR_8$; $R_8$ represents a hydrogen atom, a (C1-C10) alkyl group, or a (C6-C10) aryl group optionally having a substituent; L represents a linker; p represents 0 or 1; $R_6$ represents a (C1-C10) alkyl group optionally having a substituent, a (C6-C10) aryl group optionally having a substituent, or a (C7-C15) aralkyl group optionally having a substituent; $R_7$ represents a residue obtained by eliminating H from the substituent representing $R_6$, or a cyclic structure formed by $R_6$ and $R_7$ bonded together; $A_1$, $A_2$, and $A_3$ each represent a ligand of the platinum complex; and $Z^-$ represents a counter anion];

at least one of $R_4$ represents a substituent coordinate-bonded to the platinum complex represented by General Formula (III); $R_5$ represents a substituent selected from the group consisting of a (C1-C30) alkoxy group, a (C1-C30) aralkyloxy group, a (C6-C10) aryloxy group, a (C1-C30) alkylamino group optionally having a substituent, a di(C1-C30) alkylamino group optionally having a substituent, a substituent represented by the following General Formula (IV) obtained by eliminating H from an α-amino group of an α-amino acid derivative:

[Chemical Formula 4]

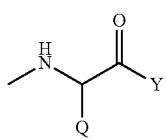
(IV)

[wherein Q represents a residue of an α-amino acid; Y represents a substituent selected from the group consisting of an amino group having a (C1-C10) alkyl group optionally having a substituent or a benzyl group optionally having a substituent, a (C1-C10) alkoxy group optionally having a phenyl group, a (C6-C10) aryloxy group, and $-NR_{12}CONHR_{13}$; and $R_{12}$ and $R_{13}$, optionally either identical or different, each represent a (C3-C6) cyclic alkyl group or a (C1-C5) alkyl group optionally being substituted with a tertiary amino group], and $-NR_9CONHR_{10}$;

$R_9$ and $R_{10}$, optionally either identical or different, each represent a (C3-C6) cyclic alkyl group or a (C1-C5) alkyl group optionally being substituted with a tertiary amino group; a represents an integer from 5 to 11,500; d, e, f, g, h, i, and j each represent an integer from 0 to 200; d+e represents an integer from 1 to 200; d+e+f+g+h+i+j represents an integer from 2 to 200; and the order of bonding of the various constituent units of polyaspartic acid is random.

(3) The polymer conjugate of a platinum(II) complex according to (2), wherein $R_1$ represents a (C1-C3) alkyl group optionally having a substituent; $R_2$ represents a (C2-C6) alkylene group; $R_3$ represents a (C1-C3) acyl group; a represents an integer from 10 to 2,000; d, e, f, g, h, i, and j each represent an integer from 0 to 100; d+e represents an integer from 1 to 100; and d+e+f+g+h+i+j represents an integer from 4 to 100.

(4) The polymer conjugate of a platinum(II) complex according to (2) or (3), wherein $R_1$ represents a methyl group; $R_2$ represents a trimethylene group; $R_3$ represents an acetyl group; $R_4$ represents a substituent selected from the group consisting of substituents represented by the following Formula (V):

[Chemical Formula 5]

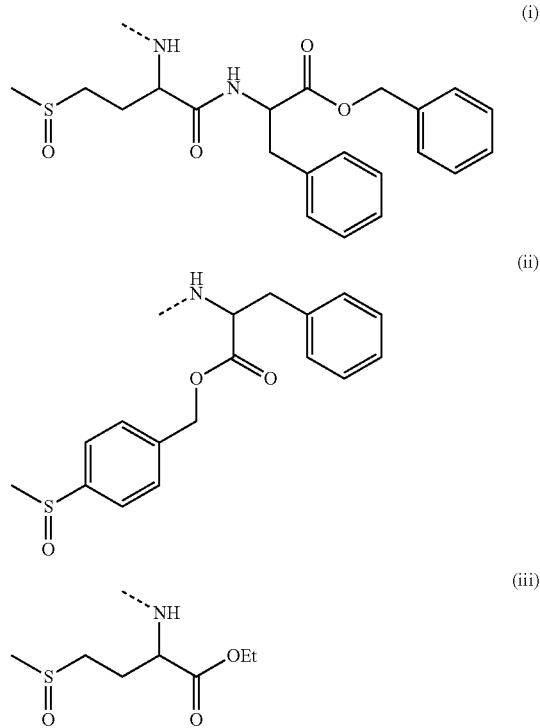

(iv)
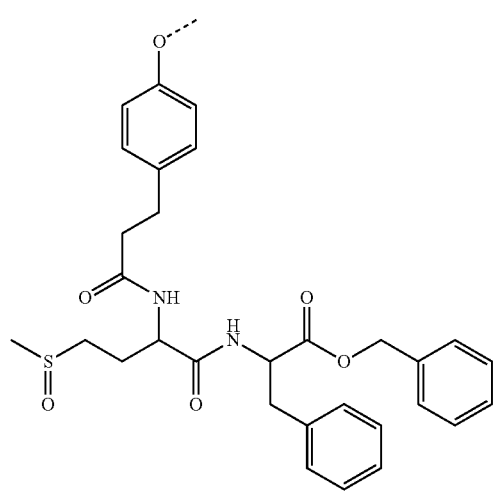
(v)
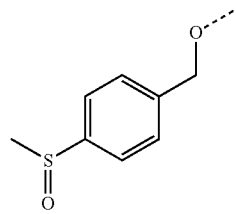
(vi)
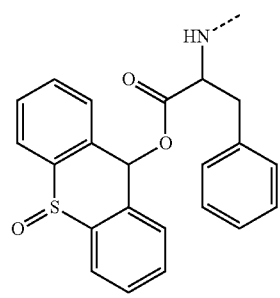
(vii)
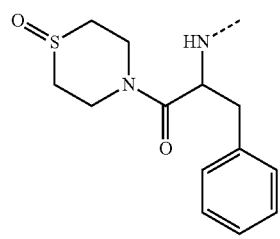
(viii)
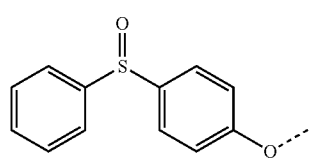
(ix)
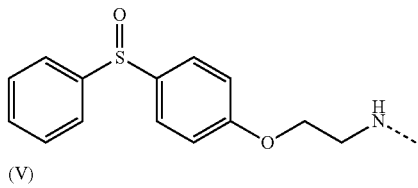
(x)
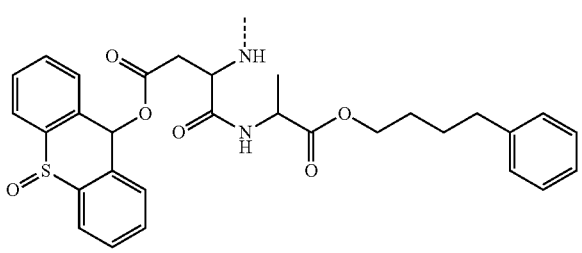
or a substituent selected from the group of substituents represented by the following Formula (VI):
[Chemical Formula 6]
(i')
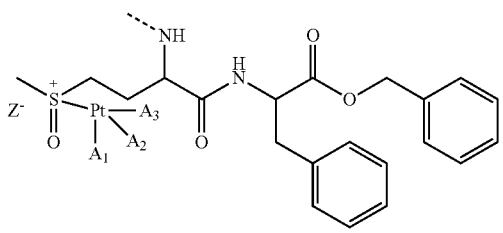
(ii')
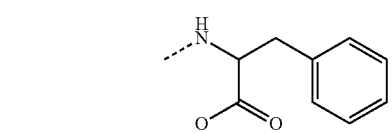
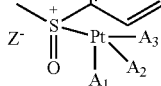
(iii')
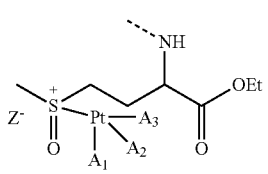

-continued (iv')

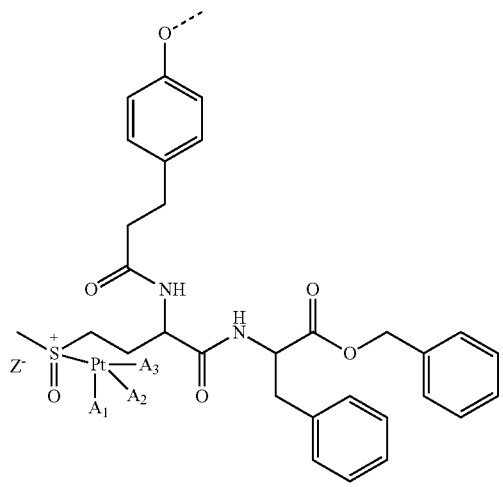

(v')

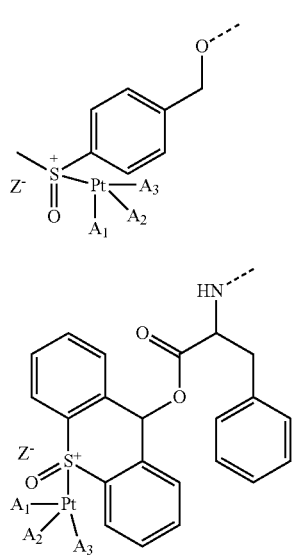

(vi')

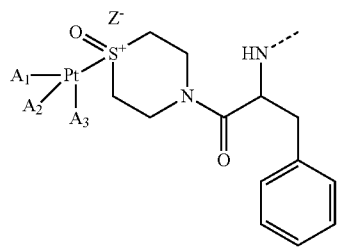

(vii')

-continued (viii')

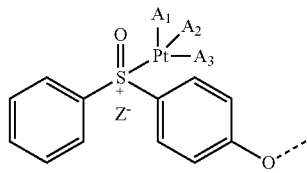

(ix')

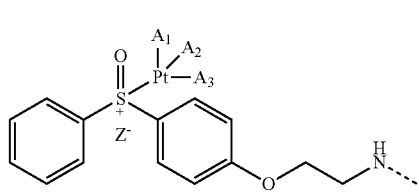

(x')

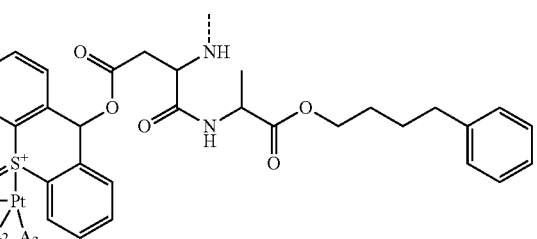

wherein $A_1$, $A_2$, $A_3$, and $Z^-$ respectively have the same meanings as described above;

at least one of $R_4$ represents a substituent coordinate-bonded to the platinum complex represented by Formula (VI); $R_5$ represents a substituent of General Formula (IV) with a benzyl group as Q, or —$NR_9CONHR_{10}$; and $R_9$ and $R_{10}$ both represent a cyclohexyl group or an isopropyl group.

(5) The polymer conjugate of a platinum(II) complex according to (1), wherein the polymer conjugate is represented by the following General Formula (VII):

[Chemical Formula 7]

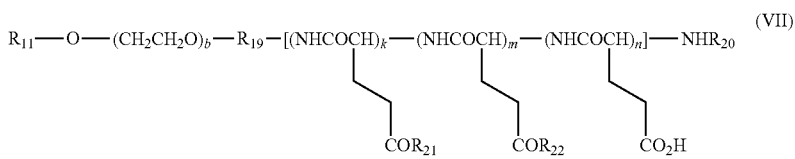

wherein $R_{11}$ represents a hydrogen atom, a (C1-C10) alkyl group optionally having a substituent, or a (C6-C10) aryl group optionally having a substituent; $R_{19}$ represents a bonding group; $R_{20}$ represents a hydrogen atom or a (C1-C6) acyl group; $R_{21}$ represents a substituent represented by the following General Formula (VIII):

[Chemical Formula 8]

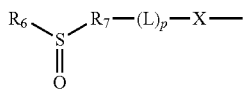 (VIII)

[wherein X represents an oxygen atom or $NR_8$; $R_8$ represents a hydrogen atom, a (C1-C10) alkyl group, or a (C6-C10) aryl group optionally having a substituent; L represents a linker; p represents 0 or 1; $R_6$ represents a (C1-C10) alkyl group optionally having a substituent, a (C6-C10) aryl group optionally having a substituent, or a (C7-C15) aralkyl group optionally having a substituent; and $R_7$ represents a residue obtained by eliminating H from the substituent representing $R_6$, or a cyclic structure formed by $R_6$ and $R_7$ bonded together], or the following General Formula (IX):

[Chemical Formula 9]

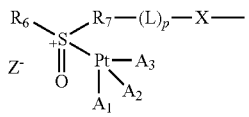 (IX)

[wherein X represents an oxygen atom or $NR_8$; $R_8$ represents a hydrogen atom, a (C1-C10) alkyl group, or a (C6-C10) aryl group optionally having a substituent; L represents a linker; p represents 0 or 1; $R_6$ represents a (C1-C10) alkyl group optionally having a substituent, a (C6-C10) aryl group optionally having a substituent, or a (C7-C15) aralkyl group optionally having a substituent; $R_7$ represents a residue obtained by eliminating H from the substituent representing $R_6$, or a cyclic structure formed by $R_6$ and $R_7$ bonded together; $A_1$, $A_2$, and $A_3$ each represent a ligand of the platinum complex; and $Z^-$ represents a counter anion];

at least one of $R_{21}$ represents a substituent coordinate-bonded to the platinum complex represented by General Formula (IX); $R_{22}$ represents a substituent selected from the group consisting of a (C1-C30) alkoxy group, a (C1-C30) aralkyloxy group, a (C6-C10) aryloxy group, a (C1-C30) alkylamino group optionally having a substituent, a di(C1-C30) alkylamino group optionally having a substituent, a substituent represented by the following General Formula (X) obtained by eliminating H from an α-amino group of an α-amino acid derivative:

[Chemical Formula 10]

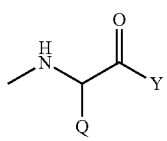 (X)

[wherein Q represents a residue of an α-amino acid; Y represents a substituent selected from the group consisting of an amino group having a (C1-C10) alkyl group optionally having a substituent or a benzyl group optionally having a substituent, a (C1-C10) alkoxy group optionally having a phenyl group, (C6-C10) aryloxy group, and —$NR_{12}CONHR_{13}$; and $R_{12}$ and $R_{13}$, being either identical or different, each represent a (C3-C6) cyclic alkyl group or a (C1-C5) alkyl group optionally substituted with a tertiary amino group], and —$NR_9CONHR_{10}$;

$R_9$ and $R_{10}$, being either identical or different, each represent a (C3-C6) cyclic alkyl group or a (C1-C5) alkyl group optionally substituted with a tertiary amino group; b represents an integer from 5 to 11,500; k represents an integer from 1 to 200; m and n each represent an integer from 0 to 200; k+m+n represents an integer from 2 to 200; and the order of bonding of the various constituent units of the polyglutamic acid is random.

(6) The polymer conjugate of a platinum(II) complex according to (5), wherein $R_{11}$ represents a (C1-C3) alkyl group optionally having a substituent; $R_{19}$ represents a (C2-C6) alkylene group, $R_{20}$ represents a (C1-C3) acyl group; b represents an integer from 10 to 2,000; k represents an integer from 1 to 100; m and n each represent an integer from 0 to 100; and k+m+n represents an integer from 3 to 100.

(7) The polymer conjugate of a platinum(II) complex according to (5) or (6), wherein $R_{11}$ represents a methyl group, $R_{19}$ represents a trimethylene group, $R_{20}$ represents an acetyl group, $R_{21}$ represents a substituent selected from the group consisting of substituents represented by the following Formula (XI):

[Chemical Formula 11]

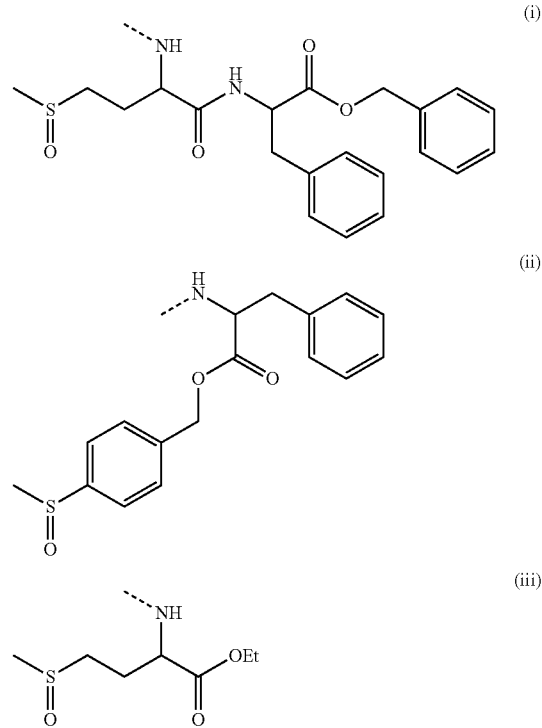

(iv)
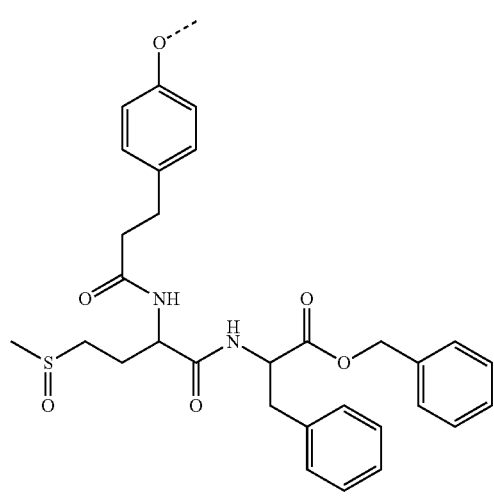
(v)
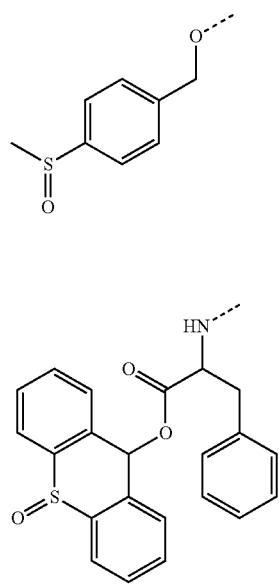
(vi)
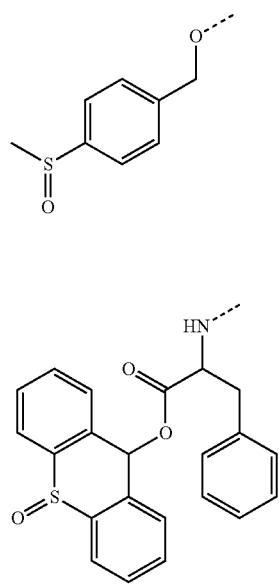
(vii)
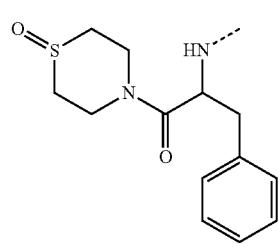
(viii)
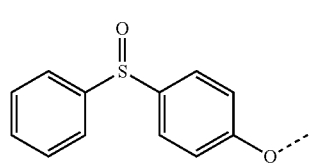
(ix)
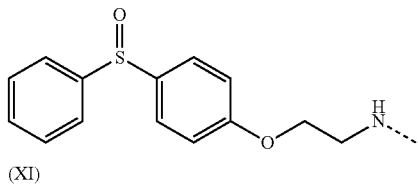
(x)
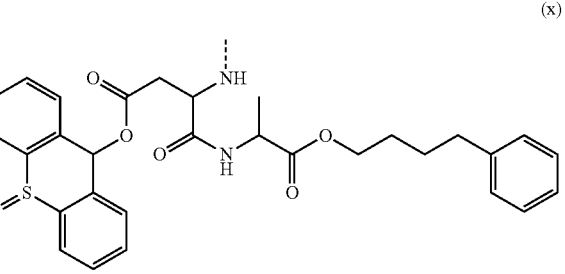
or a substituent selected from the group of substituents represented by the following Formula (XII):
[Chemical Formula 12]
(i')
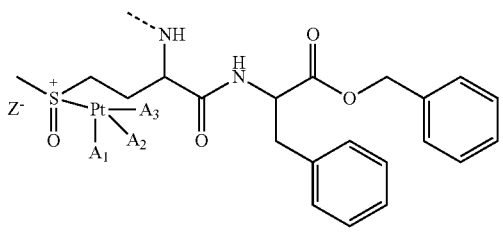
(ii')
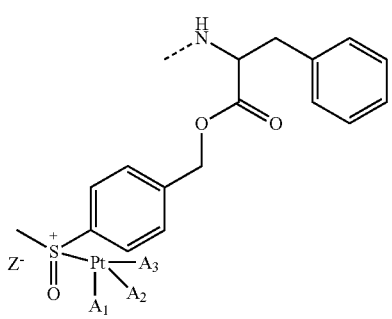
(iii')
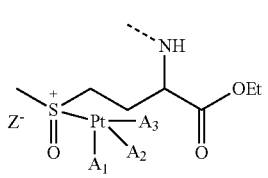

(iv')
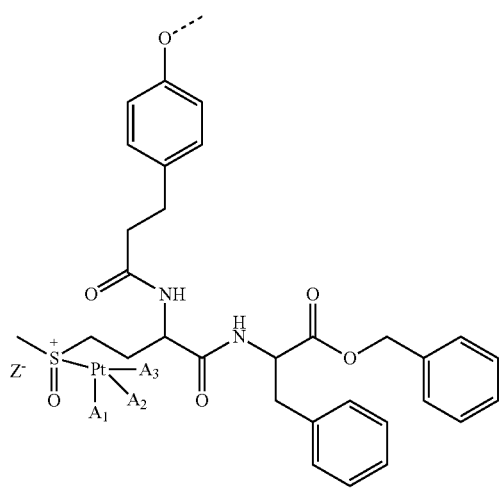

(v')
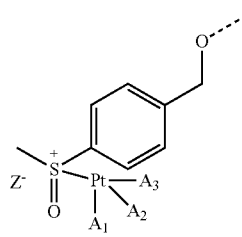

(vi')
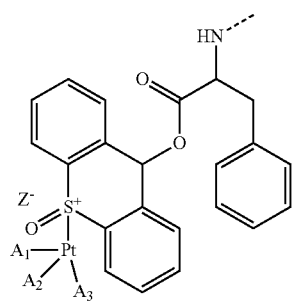

(vii')
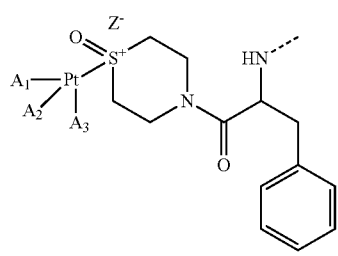

(viii')
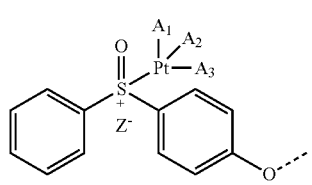

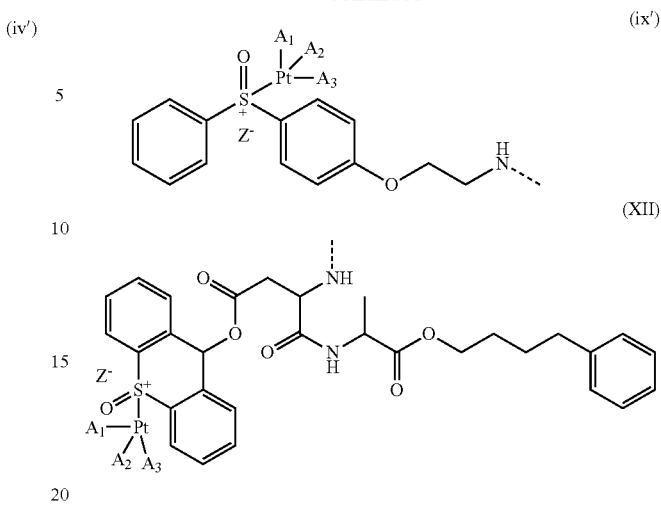

wherein $A_1$, $A_2$, $A_3$, and $Z^-$ respectively have the same meanings as described above;

provided that at least one of $R_{21}$ represents a substituent coordinate-bonded to the platinum complex represented by Formula (XII); $R_{22}$ represents a substituent of General Formula (X) with a benzyl group as Q, or —$NR_9CONHR_{10}$; and $R_9$ and $R_{10}$ both represent a cyclohexyl group or an isopropyl group.

(8) The polymer conjugate of a platinum(II) complex according to any one of (2) to (7), wherein the ligands $A_1$ and $A_2$ of the platinum complex both represent ammonia or a primary, secondary or tertiary amine, or are bonded together to form a non-cyclic or cyclic diamine optionally having a substituent; and $A_3$ represents a halogen atom, a water molecule, an amine optionally having a substituent, a heteroaryl compound, or a sulfoxide compound.

(9) The polymer conjugate of a platinum(II) complex according to (8), wherein the ligands $A_1$ and $A_2$ of the platinum complex both represent ammonia or a ligand selected from the group of ligands represented by the following Formula (XIII):

[Chemical Formula 13]

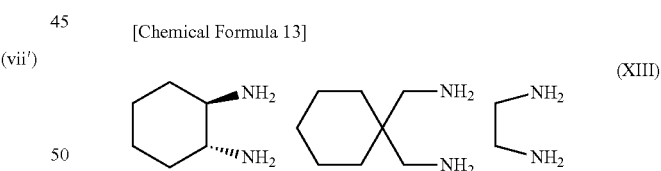

and $A_3$ represents a chlorine atom.

(10) A method for producing the polymer conjugate of a platinum(II) complex according to any one of (1) to (9), the method comprising introducing a sulfoxide derivative into a side-chain carboxyl group in a block copolymer having a polyethylene glycol structural moiety and a polyaspartic acid moiety or polyglutamic acid moiety, and then coordinate-bonding a sulfoxide group of the sulfoxide derivative to a platinum complex by ligand exchange.

(11) A medicine comprising the polymer conjugate of a platinum(II) complex according to any one of (1) to (9) as an active ingredient.

12. An antitumor agent comprising the polymer conjugate of a platinum(II) complex according to any one of (1) to (9) as an active ingredient.

Advantageous Effects of Invention

The polymer conjugate of a platinum(II) complex of the present invention, in which a polymeric sulfoxide derivative is coordinate-bonded to platinum, is positively charged and is therefore rapidly taken in by cells that are negatively charged. Thus, a medicine containing the polymer conjugate as an active ingredient provides a pharmaceutical preparation which exhibits effective antitumor activity with reduced side effect in clinical treatment. Furthermore, the polymer conjugate of a platinum(II) complex of the present invention is expected to show satisfactory stability in blood and to release the drug at a tumor site.

DESCRIPTION FOR CARRYING OUT EMBODIMENTS

The details of the present invention will be described below.

The present invention relates to a polymer conjugate of a platinum(II) complex, in which a sulfoxide group of a sulfoxide derivative that has been introduced into a side-chain carboxyl group of a block copolymer having a polyethylene glycol structural moiety and a polyaspartic acid moiety, or a polyethylene glycol structural moiety and a polyglutamic acid moiety, is coordinate-bonded to platinum.

The polyethylene glycol structural moiety according to the present invention is a polyethylene glycol having both terminals modified or having a single modified terminal, and the modifying groups at the two terminals may be identical or different. Examples of the terminal modifying group include a methyl group, an ethyl group, a n-propyl group, an isopropyl group, a n-butyl group, a s-butyl group, a t-butyl group, a benzyl group, a 4-phenylbutyl group, a dimethoxyethyl group, a diethoxyethyl group, an aminoethyl group, an aminopropyl group, and an aminobutyl group. Among them, preferred examples include a methyl group, an ethyl group, a n-propyl group, an isopropyl group, a dimethoxyethyl group, an aminoethyl group, and an aminopropyl group.

The molecular weight of the polyethylene glycol structural moiety of the block copolymer is usually about 200 to 500,000, preferably about 300 to 100,000, and more preferably about 1,000 to 90,000.

The number of side-chain carboxyl groups in the polyaspartic acid moiety or polyglutamic acid moiety of the block copolymer is about 1 to 300, preferably about 2 to 200, and more preferably about 4 to 100, per molecule on the average. The number of carboxyl groups may be determined by, for example, neutralization titration using an alkali.

The platinum(II) complex according to the present invention is not particularly limited as long as the central metal atom is divalent platinum; however, a cis-coordinated complex is preferred. To the platinum(II) complex is coordinate-bonded a polymeric sulfoxide group. The moiety that is coordinate-bonded to platinum is a sulfur atom or an oxygen atom of the sulfoxide group.

The polyaspartic acid moiety according to the present invention may be a polymer of α-form or β-form, or may be a polymer of a mixture of α-form and β-form. The polyaspartic acid moiety is preferably a polymer of a mixture of α-form and β-form.

The polyglutamic acid moiety according to the present invention may be a polymer of α-form or γ-form, or may be a polymer of a mixture of α-form and γ-form. The polyglutamic acid moiety is preferably a polymer of α-form.

The polyaspartic acid moiety or polyglutamic acid moiety according to the present invention may comprise D-amino acids only or L-amino acids only, or may comprise D-amino acids and L-amino acids as an arbitrary mixture.

The quantity of conjugation between the platinum complex and the block copolymer having a polyethylene glycol structural moiety and a polyaspartic acid moiety or a polyethylene glycol structural moiety and a polyglutamic acid moiety in the polymer conjugate of a platinum(II) complex of the present invention is not particularly limited as long as the quantity is a quantity exhibiting efficacy; however, usually, the quantity of conjugation is 1% to 95%, and preferably 5% to 80%, of the total weight of the polymer conjugate.

The halogen atom according to the present invention represents a fluorine atom, a chlorine atom, a bromine atom, or an iodine atom.

The (C1-C10) alkyl group for the (C1-C10) alkyl group which may have a substituent according to the present invention is a linear, branched or cyclic (C1-C10) alkyl group, and examples of the (C1-C10) alkyl group which may have a substituent include a methyl group, an ethyl group, a n-propyl group, a n-butyl group, a n-pentyl group, a n-hexyl group, a n-octyl group, a n-decyl group, an isopropyl group, a s-butyl group, a t-butyl group, a 2,2-dimethylpropyl group, a cyclopropyl group, a cyclobutyl group, a cyclopentyl group, a cyclohexyl group, a benzyl group, a phenethyl group, a 4-phenylbutyl group, a dimethoxyethyl group, a diethoxyethyl group, a dimethoxypropyl group, a diethoxypropyl group, an aminoethyl group, a diaminoethyl group, an aminopropyl group, and an aminobutyl group. Furthermore, examples of the (C1-C3) alkyl group which may have a substituent include a methyl group, an ethyl group, a n-propyl group, an isopropyl group, a cyclopropyl group, a benzyl group, a phenethyl group, a dimethoxyethyl group, a diethoxyethyl group, a dimethoxypropyl group, a diethoxypropyl group, an aminoethyl group, a diaminoethyl group, and an aminopropyl group.

Examples of the (C6-C10) aryl group which may have a substituent according to the present invention include a phenyl group and a naphthyl group, all of which may have a substituent, and examples of the substituent include a halogen atom, a hydroxyl group, an amino group, an alkoxy group, an acyl group, and an amide group. The position of substitution of the substituent and the number of substitutions are not particularly limited.

Examples of the amino group include an amino group, a methylamino group, an ethylamino group, a n-butylamino group, an isopropylamino group, a cyclohexylamino group, a benzylamino group, a 4-phenylbutylamino group, a dimethylamino group, a diethylamino group, a di-n-butylamino group, a diisopropylamino group, a dicyclohexylamino group, a dibenzylamino group, a bisphenylbutylamino group, a N-ethylmethylamino group, a N-methylphenylamino group, and a N-methyl-4-phenylbutylamino group.

Examples of the alkoxy group include a methoxy group, an ethoxy group, a n-butoxy group, a t-butoxy group, a cyclopropyloxy group, a cyclohexyloxy group, and an adamantyloxy group.

Examples of the acyl group include a formyl group, an acetyl group, a propionyl group, and a pivaloyl group.

Examples of the amide group include an acetamide group, a benzamide group, a N-methylacetamide group, and a N-methylbenzamide group.

The polymer conjugate of a platinum(II) complex of the present invention, in which a sulfoxide group of a sulfoxide derivative introduced into a side-chain carboxyl group in a block copolymer having a polyethylene glycol structural moiety and a polyaspartic acid moiety is coordinate-bonded to platinum, is represented by, for example, General Formula (I).

Regarding the (C1-C10) alkyl group which may have a substituent for $R_1$ of General Formula (I), the groups listed above as examples may be mentioned, and among them, a (C1-C3) alkyl group which may have a substituent is preferred, while a methyl group is particularly preferred.

Regarding the (C6-C10) aryl group which may have a substituent for $R_1$ of General Formula (I), the groups listed above as examples may be mentioned.

Examples of the bonding group represented by $R_2$ of General Formula (I) include a linear or branched (C2-C6) alkylene group. Above all, a linear (C2-C4) alkylene group is preferred, and examples thereof include an ethylene group, a trimethylene group, and a tetramethylene group, while a trimethylene group is particularly preferred.

Examples of the (C1-C6) acyl group for $R_3$ of General Formula (I) include a formyl group, an acetyl group, a propionyl group, and a pivaloyl group, and a (C1-C3) acyl group is preferred, while an acetyl group is particularly preferred.

$R_4$ of General Formula (I) represents the substituent of General Formula (II) or (III), and at least one of $R_4$ represents a substituent that is coordinate-bonded to the platinum (II) complex represented by General Formula (III).

In a case in which the sulfur atoms of the sulfoxide groups of General Formulae (II) and (III) are asymmetric centers, the compound may be a single compound or a mixture of stereoisomers.

X of General Formulae (II) and (III) represents an oxygen atom or $NR_8$, and $R_8$ represents a hydrogen atom, a (C1-C10) alkyl group, or a (C6-C10) aryl group which may have a substituent.

The (C1-C10) alkyl group for $R_8$ of General Formulae (II) and (III) is a linear, branched or cyclic (C1-C10) alkyl group, and examples thereof include a methyl group, an ethyl group, a n-propyl group, a n-butyl group, a n-pentyl group, a n-hexyl group, a n-octyl group, a n-decyl group, an isopropyl group, a s-butyl group, and a t-butyl group. Above all, a methyl group, an ethyl group, a n-propyl group, and a n-butyl group are preferred.

Regarding the (C6-C10) aryl group which may have a substituent for $R_8$ of General Formulae (II) and (III), the groups listed above as examples may be mentioned, and above all, a phenyl group is preferred.

X of General Formulae (II) and (III) is particularly preferably an oxygen atom, or NH in which $R_8$ is a hydrogen atom.

L of General Formulae (II) and (III) represents a linker, and this is a group that links $R_7$ with X and is a group which may have a linear or cyclic alkyl structure, an ester structure, an amide structure, an ether structure, a sulfide structure, a disulfide structure, or the like and may further have a substituent. P represents 0 or 1, and when p is 0, it is meant that $R_7$ is directly bonded to X without a linker.

The linker is not particularly limited; however, the linker is a substituent to which $R_7$ and X are bonded. Examples thereof include an acetylamino group, an acetoxy group, a propionylamino group, a propionyloxy group, a phenylpropionylamino group, a phenylpropionyloxy group, a methyl group, an ethyl group, a n-butyl group, a cyclopropyl group, a cyclobutyl group, a cyclohexyl group, a methoxy group, an ethoxy group, a propoxy group, a n-butoxy group, a dimethyl sulfide group, a diethyl sulfide group, an ethyl methyl sulfide group, a dimethyl disulfide group, a diethyl disulfide group, an ethyl methyl disulfide group, and a succinic acid derivative.

The (C1-C10) alkyl group of the (C1-C10) alkyl group which may have a substituent for $R_6$ of General Formulae (II) and (III) may be a linear or branched (C1-C10) alkyl group, and examples thereof include a methyl group, an ethyl group, a n-propyl group, a n-butyl group, a n-pentyl group, a n-hexyl group, a n-octyl group, a n-decyl group, an isopropyl group, a s-butyl group, a t-butyl group, and a 2,2-dimethylpropyl group. Among them, a methyl group, an ethyl group, a n-propyl group, and a n-butyl group are preferred.

The substituent is not particularly limited; however, examples include a (2-benzyloxycarbonyl)phenethylaminocarbonyl group (a group in which phenylalanine benzyl ester is amide-bonded to a carbonyl group), and an ethoxycarbonyl group.

Regarding the (C6-C10) aryl group which may have a substituent for $R_6$ of General Formulae (II) and (III), the substituents listed above as examples may be mentioned, and above all, an unsubstituted phenyl group and an unsubstituted naphthyl group are preferred.

The (C7-C15) aralkyl group which may have a substituent for $R_6$ of General Formulae (II) and (III) is a linear or branched alkyl group to which a phenyl group or a naphthyl group is bonded, and examples thereof include a benzyl group, a phenethyl group, a naphthylmethyl group, and a naphthylethyl group.

$R_7$ of General Formulae (II) and (III) is a residue obtained by eliminating H (hydrogen atom) from the substituent mentioned as $R_6$, and preferred groups are also similar to the case of $R_6$. The position of substitution of H to be eliminated is not particularly limited.

The cyclic structure formed by $R_6$ and $R_7$ bonded together in General Formulae (II) and (III) is preferably a 3-membered ring to 8-membered ring structure, and may contain heteroatoms such as an oxygen atom, a sulfur atom, a nitrogen atom, and a phosphorus atom as the constituent atoms of the ring structure. Above all, a cyclic structure which is a 5-membered ring, 6-membered ring, or 7-membered ring structure and does not contain any heteroatom, or a 5-membered ring or 6-membered ring structure containing a nitrogen atom as a heteroatom is preferred. The heteroatom may be an atom that constitutes a part of the linker. Even in a case in which a ring structure is adopted, $R_6$ and $R_7$ may have a substituent.

A preferred example of the group represented by General Formula (II) may be a group having a structure represented by the following General Formula (XIV). Meanwhile, the bond between the group of (XIV) and a side-chain carboxyl group of the block copolymer is indicated with a broken line.

[Chemical Formula 14]

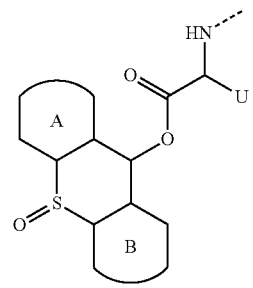

(XIV)

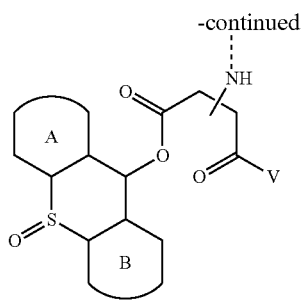

wherein ring A and ring B, which may be identical or different, each represent a carbocyclic ring having a 5-membered ring or 7-membered ring, which may have a substituent; U represents a residue of an α-amino acid; and V represents a substituent obtained by eliminating H from the amino group of an α-amino acid having a protected carboxyl group.

The carbocyclic ring of a 5-membered ring to 7-membered ring which may have a substituent, of General Formula (XIV) may have an unsaturated bond in the ring that is fused with thiopyrane oxide. Examples of the substituent include a lower alkyl group, an acyl group, and a halogen atom; however, an unsubstituted carbocyclic ring is preferred. Thioxanthene oxide in which ring A and ring B are both a benzene ring is particularly preferred.

U of General Formula (XIV) is a side chain of an essential amino acid, and examples thereof include a hydrogen atom, a methyl group, a benzyl group, and an isobutyl group. A benzyl group is particularly preferred. The α-amino acid may comprise D-amino acids only or L-amino acids only, or may comprise an arbitrary mixture of D-amino acids and L-amino acids, in one molecule or between molecules.

Examples of the α-amino acid for V of General Formula (XIV) include glycine, alanine, phenylalanine, and isoleucine, and examples of the protective group for a carboxyl group include an amino group having a benzyl group or a (C1-C10) alkyl group which may have a substituent, a (C1-C10) alkoxy group which may have a phenyl group, and a (C6-C10) aryloxy group. Among them, a substituent obtained by eliminating H from an amino group of alanine 4-phenylbutyl alcohol ester is particularly preferred.

Meanwhile, —OCOCH—U and —OCOCH$_{(1 \text{ or } 2)}$CH$_{(2 \text{ or } 1)}$CO—V of General Formula (XIV) corresponds to a linker.

Examples of the group represented by General Formula (II) include groups represented by (i) to (x) of General Formula (V) described above. Meanwhile, the bond between the group of (XIV) and a side-chain carboxyl group of the block copolymer is indicated by a broken line.

Preferred examples of the group represented by General Formula (III) include groups having the structures represented by the following General Formula (XV). Meanwhile, the bond between the group of (XV) and a side-chain carboxyl group of the block copolymer is indicated by a broken line.

[Chemical Formula 15]

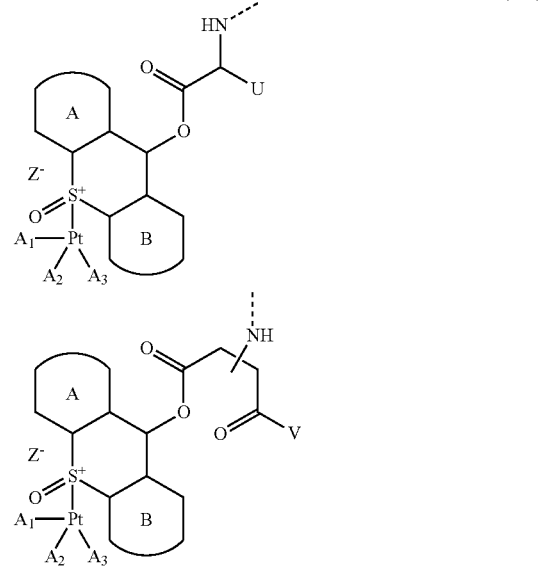

(XV)

wherein ring A and ring B, which may be identical or different, each represent a carbocyclic ring of a 5-membered ring to 7-membered ring which may have a substituent; U represents a residue of an α-amino acid; V represents a substituent obtained by eliminating H from an amino group of an α-amino acid having a protected carboxyl group; $A_1$, $A_2$, and $A_3$ each represent a ligand of a platinum complex; and $Z^-$ represents a counter anion.

Ring A, ring B, U, and V of General Formula (XV) are similar to ring A, ring B, U, and V of General Formula (XIV), and preferred groups are also similar. The portion corresponding to the linker is also similar.

$A_1$, $A_2$, and $A_3$ of General Formula (III) or General Formula (XV) each represent a ligand of a platinum complex and are not particularly limited. However, $A_1$ and $A_2$, which may be identical or different, each represent ammonia or a primary, secondary or tertiary amine, or $A_1$ and $A_2$ may be joined together to form a non-cyclic or cyclic diamine which may have a substituent, and $A_3$ is preferably a halogen atom, a water molecule, an amine which may have a substituent, a heteroaryl compound, or a sulfoxide compound. Examples of the primary, secondary or tertiary amine include methylamine, ethylamine, n-butylamine, isopropylamine, cyclohexylamine, benzylamine, 4-phenylbutylamine, dimethylamine, diethylamine, di-n-butylamine, diisopropylamine, dicyclohexylamine, dibenzylamine, bisphenylbutylamine, N-ethylmethylamine, N-methylisopropylamine, and N-cyclohexylmethylamine.

Examples of the heteroaryl compound include pyridine, quinoline, and phenanthridine, and a nitrogen atom of the compound is coordinated to platinum.

Examples of the sulfoxide compound include dimethyl sulfoxide, diethyl sulfoxide, diphenyl sulfoxide, methyl phenyl sulfoxide, methyl tolyl sulfoxide, benzyl methyl sulfoxide, and dibenzyl sulfoxide.

Regarding $A_1$, $A_2$, and $A_3$ of General Formula (III), it is more preferable that $A_1$ and $A_2$ both represent ammonia or a ligand selected from General Formula (XIII), and $A_3$ is a chlorine atom.

Examples of the group represented by General Formula (III) include groups represented by (i') to (x') of General Formula (VI). Meanwhile, the bond between the group of (VI) and a side-chain carboxyl group of the block copolymer is indicated by a broken line.

Z— of General Formula (III) or General Formula (XV) is a counter anion of platinum cation and is not particularly limited. Various ions produced by conventional salt-forming reactions may be used as necessary. Although the counter anion is described as Z— in the present invention, the counter anion is not limited to a monovalent anion and may be a polyvalent anion. Examples of the counter anion include trifluoromethylsulfonate ion ($-OSO_2CF_3$), chloride ion ($Cl^-$), nitrate ion ($NO_3^-$), phosphate ion ($HPO_4^{2-}$), sulfate ion ($SO_4^{2-}$), and hydrogen carbonate ion ($HCO_3^-$).

$R_5$ of General Formula (I) represents a substituent selected from the group consisting of a (C1-C30) alkoxy group, a (C1-C30) aralkyloxy group, a (C6-C10) aryloxy group, a (C1-C30) alkylamino group which may have a substituent, a di(C1-C30) alkylamino group which may have a substituent, an α-amino acid derivative represented by General Formula (IV), and $-NR_9CONHR_{10}$, and $R_9$ and $R_{10}$, which may be identical or different, each represent a (C3-C6) cyclic alkyl group or a (C1-C5) alkyl group which may be substituted with a tertiary amino group.

Examples of the (C1-C30) alkoxy group include a methoxy group, an ethoxy group, a n-butoxy group, a t-butoxy group, a cyclopropyloxy group, a cyclohexyloxy group, and an adamantyloxy group, and above all, an ethoxy group and a t-butoxy group are preferred.

Examples of the (C1-C30) aralkyloxy group include a benzyloxy group, a 2-phenylethoxy group, a 3-phenylpropoxy group, and a 4-phenylbutoxy group, and above all, a benzyloxy group and a 4-phenylbutoxy group are preferred.

Examples of the (C6-C10) aryloxy group include a phenoxy group and a naphthoxy group.

Examples of the (C1-C30) alkylamino group which may have a substituent and the di(C1-C30) alkylamino group which may have a substituent include a methylamino group, an ethylamino group, a n-butylamino group, an isopropylamino group, a cyclohexylamino group, a benzylamino group, a 4-phenylbutylamino group, a dimethylamino group, a diethylamino group, a di-n-butylamino group, a diisopropylamino group, a dicyclohexylamino group, a dibenzylamino group, a bisphenylbutylamino group, a N-ethylmethylamino group, a N-methylphenylamino group, and a N-methyl-4-phenylbutylamino group. Above all, an ethylamino group, a benzylamino group, and a 4-phenylbutylamino group are preferred.

Examples of the (C3-C6) cyclic alkyl group include a cyclopropyl group, a cyclobutyl group, a cyclopentyl group, and a cyclohexyl group, and above all, a cyclohexyl group is preferred. Furthermore, examples of the (C1-C5) alkyl group which may be substituted with a tertiary amino group include a methyl group, an ethyl group, a n-propyl group, a n-butyl group, a n-pentyl group, an isopropyl group, a dimethylaminopropyl group, and a 2-morpholinoethyl group. Above all, an isopropyl group and a dimethylaminopropyl group are preferred.

Q of the α-amino acid derivative represented by General Formula (IV) is preferably a side-chain of an essential amino acid, and examples include a hydrogen atom, a methyl group, a benzyl group, and an isobutyl group. A benzyl group, which is a side chain of phenylalanine, is particularly preferred. The α-amino acid derivative may comprise D-amino acids only or L-amino acids only, or may comprise an arbitrary mixture of D-amino acids and L-amino acids.

Examples of the (C1-C10) alkyl group which may have a substituent for Y include the substituents listed above as examples, and among them, a methyl group, an ethyl group, a phenyl group, a benzyl group, and a 4-phenylbutyl group are preferred.

Examples of the (C1-C10) alkoxy group which may have a phenyl group for Y include a methoxy group, an ethoxy group, a n-propoxy group, an isopropoxy group, a t-butoxy group, a benzyloxy group, a phenethyloxy group, and a 4-phenylbutoxy group.

Examples of the (C6-C10) aryloxy group for Y include a phenoxy group and a naphthoxy group.

In a case in which Y is $-NR_{12}CONHR_{13}$, examples of the (C3-C6) cyclic alkyl group and the (C1-C5) alkyl group which may be substituted with a tertiary amino group for $R_{12}$ and $R_{13}$ include groups similar to the groups listed for $R_9$ and $R_{10}$ in $R_5$ of General Formula (I) described above, and preferred groups are also similar.

Among them, Y is particularly preferably a benzyloxy group.

The substituents for $R_4$ and $R_5$ of General Formula (I) may be identical or different in one molecule, and may be substituents of a single kind or of a mixture between the molecules of the polymer conjugate of a platinum complex.

The substituent for $R_5$ of General Formula (I) is particularly preferably a residue obtained by eliminating H from an amino group of phenylalanine benzyl ester and/or $-NR_9CONHR_{10}$ (wherein $R_9$ and $R_{10}$ both represent a cyclohexyl group or an isopropyl group).

a of General Formula (I) represents an integer from 5 to 11,500, and is preferably 10 to 2,000.

d, e, f, g, h, i, and j of General Formula (I) each represent an integer from 0 to 200, d+e represents an integer from 1 to 200, and d+e+f+g+h+i+j represents an integer from 2 to 200. Preferably, d, e, f, g, h, i, and j each represent an integer from 0 to 100, d+e represents an integer from 1 to 100, and d+e+f+g+h+i+j represents an integer from 4 to 100.

In regard to the conjugate of the platinum(II) complex represented by General Formula (I) with a polymeric sulfoxide derivative, the order of bonding of the various constituent units of polyaspartic acid is random.

The polymer conjugate of a platinum(II) complex in which a sulfoxide group of a sulfoxide derivative introduced into a side-chain carboxyl group in a block copolymer having a polyethylene glycol structural moiety and a polyglutamic acid moiety is coordinate-bonded to platinum, is represented by, for example, General Formula (VII) described above.

Examples of the (C1-C10) alkyl group which may have a substituent for $R_{11}$ of General Formula (VII) include groups similar to the (C1-C10) alkyl group which may have a substituent for $R_1$ of General Formula (I), and preferred groups are also similar.

Examples of the (C6-C10) aryl group which may have a substituent for $R_{11}$ of General Formula (VII) include groups similar to the (C6-C10) aryl group which may have a substituent for $R_1$ of General Formula (I).

Examples of the bonding group represented by $R_{19}$ of General Formula (VII) include groups similar to the bonding group for $R_2$ of General Formula (I), and preferred groups are also similar.

Examples of the (C1-C6) acyl group for $R_{20}$ of General Formula (VII) include groups similar to the (C1-C6) acyl group for $R_3$ of General Formula (I), and preferred groups are also similar.

$R_{21}$ of General Formula (VII) represents a substituent of General Formula (VIII) or (IX), and at least one of $R_{21}$ represents a substituent to which a platinum(II) complex represented by General Formula (IX) is coordinate-bonded.

In a case in which the sulfur atom of a sulfoxide group of General Formulae (VIII) and (IX) is an asymmetric center, the compound may be a single compound or a mixture of stereoisomers.

Examples of X of General Formulae (VIII) and (IX) include groups similar to X of General Formulae (II) and (III), and preferred groups are also similar.

Examples of $R_8$ of General Formulae (VIII) and (IX) include groups similar to $R_8$ of General Formulae (II) and (III), and preferred groups are also similar.

L of General Formulae (VIII) and (IX) represents a linker, and examples thereof include groups similar to L of General Formulae (II) and (III). Furthermore, p is also similar to p of General Formulae (II) and (III).

Examples of the (C1-C10) alkyl group which may have a substituent for $R_6$ of General Formulae (VIII) and (IX) include groups similar to the (C1-C10) alkyl group which may have a substituent for $R_6$ of General Formulae (II) and (III), and preferred groups are also similar. The substituents are also the same as described above.

Examples of the (C6-C10) aryl group which may have a substituent for $R_6$ of General Formulae (VIII) and (IX) include groups similar to the (C6-C10) aryl group which may have a substituent for $R_6$ of General Formulae (II) and (III), and preferred groups are also similar.

Examples of the (C7-C15) aralkyl group which may have a substituent for $R_6$ of General Formulae (VIII) and (IX) include groups similar to the (C7-C15) aralkyl group which may have a substituent for $R_6$ of General Formulae (II) and (III), and preferred groups are also similar.

$R_7$ of General Formulae (VIII) and (IX) is similar to $R_7$ of General Formulae (II) and (III), and preferred groups are also similar.

The cyclic structure formed by $R_6$ and $R_7$ bonded together in General Formulae (VIII) and (IX) is preferably a 3-membered ring to 8-membered ring structure, and may contain a heteroatom such as an oxygen atom, a sulfur atom, a nitrogen atom, or a phosphorus atom as a constituent atom of the ring structure. Above all, a cyclic structure that is a 5-membered ring, 6-membered ring, or 7-membered ring structure and does not contain a heteroatom, or a 5-membered ring or 6-membered ring structure containing a nitrogen atom as a heteroatom is preferred. The heteroatom may be an atom that constitutes a portion of the linker. Even in a case in which $R_6$ and $R_7$ adopt a ring structure, $R_6$ and $R_7$ may have a substituent.

A preferred example of the group represented by General Formula (VIII) may be a group having a partial structure represented by General Formula (XIV), and a preferred example of the group represented by General Formula (IX) may be a group having a partial structure represented by General Formula (XV). Here, U, V, $A_1$, $A_2$, $A_3$, and $Z^-$ respectively have the same meanings as described above.

Examples of the group represented by General Formula (VIII) include groups represented by (i) to (x) of General Formula (XI), and examples of the group represented by General Formula (IX) include groups represented by (i') to (x') of General Formula (XII). Meanwhile, the bond between the group of (XII) and a side-chain carboxyl group of the block copolymer is indicated by a broken line.

$A_1$, $A_2$, and $A_3$ of General Formula (IX) represent ligands of the platinum complex, and examples include groups similar to $A_1$, $A_2$, and $A_3$ of General Formula (III). Preferred groups are also similar.

Examples of $Z^-$ of General Formula (IX) include ions similar to $Z^-$ of General Formula (III), and preferred ions are also similar.

$R_{22}$ of General Formula (VII) represents a group selected from the group consisting of a (C1-C30) alkoxy group, a (C1-C30) aralkyloxy group, a (C6-C10) aryloxy group, a (C1-C30) alkylamino group which may have a substituent, a di(C1-C30) alkylamino group which may have a substituent, an α-amino acid derivative represented by General Formula (X), and —$NR_9CONHR_{10}$, and $R_9$ and $R_{13}$, which may be identical or different, each represent a (C3-C6) cyclic alkyl group or a (C1-C5) alkyl group which may be substituted with a tertiary amino group.

Here, examples of the (C1-C30) alkoxy group, (C1-C30) aralkyloxy group, (C6-C10) aryloxy group, (C1-C30) alkylamino group which may have a substituent, di(C1-C30) alkylamino group which may have a substituent, (C3-C6) cyclic alkyl group, and (C1-C5) alkyl group which may be substituted with a tertiary amino group, include groups similar to the (C1-C30) alkoxy group, (C1-C30) aralkyloxy group, (C6-C10) aryloxy group, (C1-C30) alkylamino group which may have a substituent, di(C1-C30) alkylamino group which may have a substituent, (C3-C6) cyclic alkyl group, and (C1-C5) alkyl group which may be substituted with a tertiary amino group for $R_5$ of General Formula (I), respectively. Preferred groups are also similar.

Examples of Q of the α-amino acid derivative represented by General Formula (X) include groups similar to Q of the α-amino acid derivative represented by General Formula (IV), and preferred groups are also similar. Furthermore, examples of the (C3-C6) cyclic alkyl group and the (C1-C5) alkyl group which may be substituted with a tertiary amino group for $R_{12}$ and $R_{13}$ in the cases of the (C1-C10) alkyl group which may have a substituent, (C1-C10) alkoxy group which may have a phenyl group, (C6-C10) aryloxy group, and —$NR_{12}CONHR_{13}$ for Y of General Formula (X), include groups similar to the (C3-C6) cyclic alkyl group and the (C1-C5) alkyl group which may be substituted with a tertiary amino group for $R_{12}$ and $R_{13}$ in the cases of the (C1-C10) alkyl group which may have a substituent, (C1-C10) alkoxy group which may have a phenyl group, (C6-C10) aryloxy group, and —$NR_{12}CONHR_{13}$ for Y of General Formula (IV) described above. Preferred groups are also similar. Among them, Y is particularly preferably a benzyloxy group.

The substituents for $R_{21}$ and $R_{22}$ of General Formula (VII) may be identical or different in one molecule, and the substituents may be substituents of a single kind or of a mixture between the molecules of the polymer conjugate of the platinum complex.

Particularly preferred examples of the substituent for $R_{22}$ of General Formula (VII) include a residue obtained by eliminating H from an amino group of phenylalanine benzyl ester and/or —$NR_9CONHR_{10}$ (wherein $R_9$ and $R_{10}$ both represent a cyclohexyl group or an isopropyl group).

b of General Formula (VII) represents an integer from 5 to 11,500, and b is preferably 10 to 2,000.

k of General Formula (VII) represents an integer from 1 to 200, m and n each represent an integer from 0 to 200, and k+m+n represents an integer from 2 to 200. Preferably, k represents an integer from 1 to 100, m and n each represent an integer from 0 to 100, and k+m+n represents 3 to 100.

In regard to the conjugate of the platinum(II) complex represented by General Formula (VII) with a polymeric sulfoxide derivative, the order of bonding of the various constituent units of polyglutamic acid is random.

The polymer conjugate of a platinum(II) complex of the present invention, in which a polymeric sulfoxide derivative is coordinate-bonded to platinum, may be obtained by, for example, introducing a sulfoxide derivative into a side-chain carboxyl group of a block copolymer having a polyethylene glycol structural moiety and a polyaspartic acid moiety or a polyethylene glycol structural moiety and a polyglutamic acid moiety, and coordinate-bonding the sulfoxide group to a platinum(II) complex by ligand exchange in an organic solvent or an aqueous solution. The present production method is also included in the present invention.

The production method will be explained by taking the compound of General Formula (I) or General Formula (VII) as an example. Regarding a method of introducing the structure represented by General Formula (II) or (III) into $R_4$ of General Formula (I), for example, a block copolymer having a polyethylene glycol structural moiety and a polyaspartic acid moiety, which is produced by the method described in JP 3268913 B2, and a sulfoxide derivative in which functional groups other than a hydroxyl group, an amino group or the like, which are allowed to react as necessary, have been protected, are subjected to a reaction using a dehydration condensing agent such as dicyclohexylcarbodiimide (DCC), diisopropylcarbodiimide (DIPC), 1-ethyl-3-(3-dimethylaminopropyl)carbodiimide hydrochloride (WSC), or 1-ethoxycarbonyl-2-ethoxy-1,2-dihydroxyquinolinone (EEDQ) in a solvent, preferably in an aprotic polar solvent such as N,N-dimethylformamide (DMF), 1,3-dimethyl-2-imidazolidinone (DMI), or N-methylpyrrolidone (NMP), at 0 to 180° C., or preferably at 5° C. to 50° C., and thereby the sulfoxide derivative is introduced into the block copolymer. A polymeric sulfoxide derivative is produced by conventional operations for separation and purification, and the like. Furthermore, at the time of the condensation reaction, a reaction aid such as N,N-dimethylaminopyridine (DMAP) may also be used. Subsequently, the polymeric sulfoxide derivative thus obtained is dissolved in a solvent, preferably an aprotic polar solvent such as preferably N,N-dimethylformamide (DMF), 1,3-dimethyl-2-imidazolidinone (DMI), or N-methylpyrrolidone (NMP), and a solution obtained by treating DACH-platin (Pt(R,R-dach)Cl$_2$) with silver trifluoromethanesulfonate is added to the solution (see Non-Patent Literature: J. Am. Chem. Soc. 2014, 136, 2126-2134). Ligand exchange is performed at 0° C. to 180° C., and preferably 5° C. to 50° C., and thereby the sulfoxide group is bonded to platinum. In a case in which a protective group has been used, the product may be subjected to an elimination reaction according to the protective group in a stage where the reaction will not be adversely affected.

Furthermore, regarding a method of introducing a group represented by General Formula (VIII) or (IX) into $R_{21}$ in the compound of General Formula (VII), for example, the introduction may be carried out by a similar production method using a block copolymer having a polyethylene glycol structural moiety and a polyglutamic acid moiety that is produced by the method described in JP 4745664 B2 instead of the block copolymer having a polyethylene glycol structural moiety and a polyaspartic acid moiety as described above. In regard to the protective group, the same procedure as described above also applies.

Regarding a method of introducing a desirable substituent into $R_5$ or $R_{22}$ in the compound of General Formula (I) or (VII), a method of activating carboxyl groups of the block copolymer by a method used in conventional ester synthesis or amide synthesis, and then reacting the activated carboxyl groups with a corresponding alcohol, a corresponding amine, an amino acid having a protected carboxyl group, or the like in an amount that is wished to be conjugated, under basic conditions; a method of activating a corresponding alcohol, a corresponding amine, an amino acid having a protected carboxyl group, or the like, and then reacting the activated compound with carboxyl groups of the block copolymer; and the like may be used.

It is also acceptable that after the product is purified, unreacted carboxyl groups in the polymer are reactivated by a similar reaction, a sulfoxide derivative is condensed with these reactivated carboxyl groups at a hydroxyl group or amino group of the derivative. Alternatively, it is also acceptable that different alcohols, amines and the like are repeatedly reacted, thereby a compound having a mixture of various substituents for $R_5$ or $R_{22}$ is synthesized, and then a hydroxyl group or an amino group of a sulfoxide derivative is condensed with the compound thus obtained. The order of those reactions may be different from each other.

The method for producing a platinum(II) complex of the present invention, to which a polymeric sulfoxide derivative is coordinate-bonded, is not limited to these methods. Examples of the production method will be also disclosed in the Examples given below.

A medicine containing, as an active ingredient, a polymer conjugate of a platinum(II) complex coordinate-bonded to a polymeric sulfoxide derivative of the present invention is also included in the present invention. The medicine is preferably used as an antitumor agent.

Regarding the use as an antitumor agent, the polymer conjugate may be used alone, or as a mixture with pharmaceutically acceptable additives such as a carrier, an excipient, a disintegrant, a binder, a lubricating agent, a fluidizing agent, a coating agent, a suspending agent, an emulsifying agent, a stabilizer, a preservative, a corrigent, a flavoring agent, a diluents, and a dissolution aid. The polymer conjugate may be administered orally or parenterally (systemic administration, topical administration, or the like) in the form of a preparation such as a powder preparation, a granular preparation, a tablet, a caplet, a capsule, an injectable preparation, a suppository, or an ointment. Use of the polymer conjugate as an injectable preparation is particularly preferred, and usually, for example, water, a 5% glucose or mannitol solution, a water-soluble organic solvent (for example, glycerol, ethanol, N-methylpyrrolidone, polyethylene glycol, Cremophor, or a mixture thereof), a mixed liquid of water and the water-soluble organic solvent, or the like is used.

The amount of administration of the polymer conjugate as the anticancer agent may definitely vary depending on the gender, age, physiological state, pathological condition and the like of the patient; however, usually, the anticancer agent is administered parenterally at a dose of 0.01 to 1,500 mg/m$^2$, and preferably 0.1 to 250 mg/m$^2$, in terms of the active ingredient, per day for an adult. Administration by injection is performed through a vein, an artery, a diseased site (tumor site), or the like.

EXAMPLES

Hereinafter, the present invention will be described in more detail by way of Examples. However, the present invention is not intended to be limited to these Examples.

In the Examples of the present invention, the following abbreviations are used.

R,R-dach: (1R,2R)-cyclohexanediamine
1-OHP: Oxaliplatin
Boc: tert-Butoxycarbonyl group
OTf: Trifluoromethanesulfonate The drug content of a compound in the present Examples is a value obtained by measuring the platinum content using an inductively coupled plasma optical emission spectrometer, ICP-OES (manufactured by Agilent Technologies, Inc.: Model 720-ES), and calculating the content in terms of Pt(R,R-dach)Cl$_2$.

Measurement of the particle size and the zeta potential of a compound used in the present Examples was carried out using a particle size-zeta potential measuring apparatus (manufactured by Malvern Instruments, Ltd.; ZETASIZER NANO ZS).

The molecular weight of a compound used in the present Example was measured using LC/MS (Shimadzu LCMS-2020).

Column: INERTSIL ODS-3 φ 2.1 mm×100 mm
Mobile phase A: Acetonitrile/formic acid (99.9/0.1)
Mobile phase B: Water/formic acid (99.9/0.1)
Gradient:

|  | Time (minutes) | | | | |
| --- | --- | --- | --- | --- | --- |
|  | 0.0 | 5.5 | 6.5 | 6.51 | 10.0 |
| Concentration of liquid A (%) | 20 | 90 | 90 | 20 | 20 |

Flow rate: 0.3 ml/min

Reference Example 1 Synthesis of Sulfoxide Derivative (i)

N-Boc-L-methionine sulfoxide (2.5 g; manufactured by Watanabe Chemical Industries, Ltd.) and phenylalanine benzyl ester hydrochloride (3.0 g) were suspended in dichloromethane (50 ml), and DMAP (0.12 g) and triethylamine (2.3 g) were added to the suspension. The mixture was stirred at 0° C. WSC (2.17 g) was added to the reaction liquid, subsequently the temperature was gradually increased to room temperature, and the reaction liquid was stirred for 46 hours. After completion of the reaction, the reaction liquid was washed sequentially with a saturated aqueous solution of sodium hydrogen carbonate, distilled water, and saturated brine. Anhydrous sodium sulfate was added to the organic layer, a solid was filtered, and then the filtrate was concentrated under reduced pressure. A mixed liquid of acetone (50 ml) and hexane (450 ml) was added to the residue thus obtained, and a solid was precipitated out. The solid was collected by filtration and dried under reduced pressure, and thus a Boc-protected form of the title compound was obtained (3.0 g).

$^1$H-NMR (CDCl$_3$): δ7.39-7.21 (10H, m), 7.13-7.07 (2H, m), 5.19-5.10 (2H, m), 4.85-4.79 (1H, m), 4.54-4.40 (1H, m), 3.20-3.0 (3H, m), 2.61 (1.5H, s, SOMe), 2.54 (1.5H, s, SOMe), 2.60-2.52 (1H, m), 2.35-2.22 (1H, m), 2.18-2.08 (1H, m), 1.42 (9H, s).

The Boc-protected form (2.0 g) thus obtained was dissolved in dichloromethane (10 ml), and the solution was cooled to 0° C. Subsequently, trifluoroacetic acid (10 ml) was slowly added thereto, and the mixture was stirred for 2 hours at the same temperature. After completion of the reaction, the reaction liquid was concentrated under reduced pressure, and trifluoroacetate of the title compound was obtained (quant.).

Reference Example 2 Production of DMF Solution of Pt(R,R-dach)Cl(OTf)

According to the method of a Non-Patent Literature (J. Am. Chem. Soc., 2014, 136, 2126-2134), DACH-platin (Pt(R,R-dach)Cl$_2$; 1.5 g) produced by the method described in Bioorg. Med. Chem. Lett., 2006, 16, 1686-1691 was suspended in DMF (50 ml) in the dark, and a DMF solution (25 ml) of silver trifluoromethanesulfonate (1.0 g; manufactured by Tokyo Chemical Industry Co., Ltd.) was added to the suspension. Subsequently, the mixture was stirred for 20 hours at room temperature. After completion of the reaction, silver chloride produced therein was precipitated using a centrifuge, a supernatant was filtered, and thereby the title solution was produced.

Example 1 Production of compound of Example 1 (conjugate of polymeric sulfoxide derivative and platinum(II) complex, obtained by introducing sulfoxide derivative (i) into block copolymer comprising methoxy polyethylene glycol moiety having molecular weight of 12,000 and polyaspartic acid moiety having polymerization number of about 43: in General Formula (I), $R_1$=methyl group, $R_2$=trimethylene group, $R_3$=acetyl group, $R_4$=sulfoxide derivative (i) or (i'), $R_5$=isopropylaminocarbonylisopropylamino group, Z=OTf, d+e+f+g+h+i+j=about 43, a=about 273)

A methoxy polyethylene glycol-polyaspartic acid block copolymer (polymerization number of aspartic acid: about 43; 2.65 g) produced by the method described in JP 3268913 B2 and the trifluoroacetate of sulfoxide derivative (i) obtained in Reference Example 1 (2.0 g) were dissolved in DMF (70 ml) at 35° C., and then diisopropylethylamine (1.6 ml) and DMAP (81 mg) were added to the solution. The reaction liquid was adjusted to 25° C., subsequently DIPC (2.0 ml) was added thereto, and the mixture was stirred for 23 hours at the same temperature. Subsequently, DIPC (0.5 ml) was added thereto, and the mixture was stirred for another one hour. After completion of the reaction, the reaction liquid was slowly added to a mixed liquid of ethyl acetate (70 ml), ethanol (70 ml), and diisopropyl ether (560 ml), and the mixture was stirred at room temperature. Subsequently, the mixture was left to stand until a desired product precipitated and deposited, and a supernatant was removed. The deposit was collected by filtration and was subjected to drying under reduced pressure. Thus, a polymeric sulfoxide derivative (3.85 g) was obtained. The polymeric sulfoxide derivative (3.7 g) thus obtained was dissolved in DMF (20 ml) at 35° C., and then the solution was cooled to 25° C. Subsequently, the Pt(R,R-dach)Cl(OTf) solution (20 mg/ml, 58.6 ml) produced by the method described in Reference Example 2 was added to the solution, and the mixture was stirred for 24 hours at 25° C. After completion of the reaction, the reaction liquid was slowly added to a mixed liquid of ethyl acetate (80 ml), ethanol (80 ml), and diisopropyl ether (640 ml), and the mixture was stirred at room temperature. Subsequently, the mixture was left to stand until a desired product precipitated and deposited, and a supernatant was removed. The deposit was collected by filtration and was subjected to drying under reduced pressure. Thus, a crude form of the title compound (4.72 g) was obtained. The crude form (2.2 g) thus obtained was purified by cross-flow type ultrafiltration, VIVAFLOW 200 (manufactured by Sartorius AG, MWCO: 10k), and the aqueous solution obtained after purification was freeze-dried. Thus, the title compound was obtained (2.1 g). The drug content of the compound thus obtained, in terms of Pt(R,R-dach)Cl$_2$, was 20.5% (mass fraction). Furthermore, the title compound was dissolved in purified water to a concentration of 1 mg/ml, and the particle size was measured. The particle size was 85 nm, and the title compound formed micelles.

Reference Example 3 Production of block copolymer comprising methoxy polyethylene glycol moiety having molecular weight of 12,000 and moiety having structure in which phenylalanine is bonded to side chain of polyaspartic acid having polymerization number of about 43

A methoxy polyethylene glycol-polyaspartic acid block copolymer (polymerization number of aspartic acid: about 43; 0.8 g) produced by the method described in JP 3268913 B2 was dissolved in DMF (8 ml) at 35° C., and phenylalanine benzyl ester hydrochloride (0.35 g), diisopropylethylamine (0.21 ml), and DMAP (25 mg) were added to the solution. The liquid temperature was cooled to 25° C., and then DIPC (0.22 ml) was added to the liquid. The mixture was stirred for 5 hours at the same temperature. After completion of the reaction, the mixture was added dropwise to a mixed liquid of heptanes (128 ml) and ethanol (32 ml), and a solid precipitated therefrom was collected by filtration and dried under reduced pressure. Thus, a benzyl ester form of the title compound (1.0 g) was obtained. The benzyl ester form (0.95 g) thus obtained was dissolved in DMF (19 ml) at 35° C., hydrated Pd/C (10% 95 mg) was added to the solution, and the mixture was stirred for 13 hours at room temperature in a hydrogen atmosphere. After completion of the reaction, activated carbon (0.95 g) was added to the reaction mixture, and the mixture was stirred for one hour and filtered. The mother liquor thus obtained was added dropwise to a mixed liquid of ethyl acetate (40 ml) and diisopropyl ether (160 ml), and a solid precipitated therefrom was collected by filtration and then was subjected to drying under reduced pressure. Thus, the title compound (0.20 g) was obtained.

Reference Example 4 Synthesis of (4-(methylsulfinyl)phenyl)methanol (Sulfoxide Derivative (v))

The title compound was synthesized (0.49 g) by the method described in Adv. Synth. Catal., 2007, 349, 2425-2430, using (4-(methylthio)phenyl)methanol (1.54 g). The $^1$H-NMR spectrum of the compound thus obtained was coincident with the values described in the literature.

Example 2 Production of compound of Example 2 (conjugate of polymeric sulfoxide derivative and platinum complex, obtained by introducing sulfoxide derivative (ii) into block copolymer comprising methoxy polyethylene glycol moiety having molecular weight of 12,000 and polyaspartic acid moiety having polymerization number of about 43: in General Formula (I), R$_1$=methyl group, R$_2$=trimethylene group, R$_3$=acetyl group, R$_4$=sulfoxide derivative (ii) or (ii'), R$_5$=isopropylaminocarbonylisopropylamino group or 2-amino-N-isopropyl-N-(isopropylcarbamoyl)-3-phenyl-propanamide, Z=OTf, d+e+f+g+h+i+j=about 43, a=about 273)

A block copolymer (0.65 g) having a methoxy polyethylene glycol moiety and a structure in which phenylalanine was bonded to a side chain of a polyaspartic acid having a polymerization number of about 43 obtained in Reference Example 3, and the sulfoxide derivative (v) (0.14 g) obtained in Reference Example 4 were dissolved in DMF (20 ml) at 35° C., and then DMAP (20 mg) was added to the solution. The reaction liquid was adjusted to 25° C., subsequently DIPC (0.41 ml) was added thereto, and the mixture was stirred for 24.5 hours at the same temperature. Subsequently, DIPC (0.1 ml) was added thereto, and the mixture was stirred for another one hour. After completion of the reaction, the reaction liquid was slowly added to a mixed liquid of ethyl acetate (20 ml), ethanol (20 ml), and diisopropyl ether (160 ml), and the mixture was stirred at room temperature. Subsequently, the mixture was left to stand until a desired product precipitated and deposited, and a supernatant was removed. The deposit was collected by filtration and then was dried under reduced pressure, and thereby a polymeric sulfoxide derivative (0.72 g) was obtained. The polymeric sulfoxide derivative (0.7 g) thus obtained was dissolved in DMF (5 ml) at 35° C., and then the solution was cooled to 25° C. Subsequently, a Pt(R,R-dach)Cl(OTf) solution (12.5 mg/m, 15 ml) produced by the method described in Reference Example 2 was added to the solution, and the mixture was stirred for 23 hours at 25° C. After completion of the reaction, the reaction liquid was slowly added to a mixed liquid of ethyl acetate (20 ml), ethanol (20 ml), and diisopropyl ether (160 ml), and the mixture was stirred at room temperature. Subsequently, the mixture was left to stand until a desired product precipitated and deposited, and a supernatant was removed. The deposit was collected by filtration and then was dried under reduced pressure, and thereby a crude form of the title compound (0.85 g) was obtained. The crude form (0.84 g) thus obtained was purified by centrifugal ultrafiltration, VIVASPIN 20 (manufactured by Sartorius AG, MWCO: 10k), and the aqueous solution obtained after purification was freeze-dried. Thus, the title compound was obtained (0.66 g). The drug content of the compound thus obtained, in terms of Pt(R,R-dach)Cl$_2$, was 15.0% (mass fraction). Furthermore, the title compound was dissolved in purified water to a concentration of 1 mg/ml, and the particle size was measured. The particle size was 60 nm, and the title compound formed micelles.

Reference Example 5 Synthesis of Methionine Sulfoxide Ethyl Ester (Sulfoxide Derivative (iii))

N-Boc-L-methionine sulfoxide (2.00 g) was dissolved in dichloromethane (40 ml), and then ethanol (0.485 ml), DMAP (93.2 mg), and DIPC (1.32 ml) were sequentially added to the solution. The mixture was stirred overnight, and then a solid thus produced was removed by filtration. The filtrate was concentrated under reduced pressure. Subsequently, a crude form of N-Boc-L-methionine sulfoxide ethyl ester (2.84 g) was dissolved in a hydrogen chloride ethanol solution (2 mol/l, 12.4 ml), and the solution was stirred for 4 hours. The reaction liquid was concentrated under reduced pressure, and the residue was subjected to silica gel column chromatography (silica gel 36 g) with chloroform:methanol=15:1 (320 ml) so as to remove any unnecessary fractions. Subsequently, the purification product was collected with methanol and purified, and thus the title compound (743 mg) was obtained.

$^1$H-NMR (CD$_3$OD): δ4.34 (2H, q, J=7.0 Hz), 4.23 (1H, t, J=6.0 Hz), 3.19-3.03 (1H, m), 3.00-2.85 (1H, m), 2.70 (3H, s), 2.54-2.27 (2H, m), 1.34 (3H, t, J=7.0 Hz).

Example 3 Production of compound of Example 3 (conjugate of polymeric sulfoxide derivative and platinum complex, obtained by introducing sulfoxide derivative (iii) into block copolymer comprising methoxy polyethylene glycol moiety having molecular weight of 12,000 and polyaspartic acid moiety having polymerization number of about 43: in General Formula (I), $R_1$=methyl group, $R_2$=trimethylene group, $R_3$=acetyl group, $R_4$=sulfoxide derivative (iii) or (iii'), $R_5$=isopropylaminocarbonylisopropylamino group, Z=OTf, d+e+f+g+h+i+j=about 43, a=about 273)

A methoxy polyethylene glycol-polyaspartic acid block copolymer (polymerization number of aspartic acid: about 43; 742 mg) produced by the method described in JP 3268913 B2 and methionine sulfoxide ethyl ester (516 mg) obtained in Reference Example 5 were dissolved in DMF (11 ml) at 35° C., and then diisopropylethylamine (0.49 ml) was added to the solution. The reaction liquid was adjusted to 25° C., subsequently DIPC (0.60 ml) was added thereto, and after a lapse of 22 hours and 15 minutes, DIPC (0.15 ml) was added thereto. The mixture was further stirred for 1 hour and 50 minutes. The reaction liquid was added dropwise to diisopropyl ether (147 ml), and the reaction container was washed with ethyl acetate (14.7 ml) into the mixture. The mixture was stirred overnight at room temperature, and then a powder thus obtained was filtered. The powder was washed two times with diisopropyl ether (15 ml), and a crude form (1.24 g) was obtained. The crude form (1.24 g) thus obtained was dissolved in purified water (14.7 ml) at normal temperature, subsequently an ion exchange resin (manufactured by Muromachi Chemicals, Inc., MUROMAC® XSC-1114-H; 10 ml) was added to the solution, and the mixture was stirred for 1 hour and 30 minutes. The ion exchange resin was removed by filtration, and the ion exchange resin was washed two times with purified water (10 ml) into the solution. The aqueous solution thus obtained was subjected to freeze-drying, and thus a polymeric sulfoxide derivative (0.79 g) was obtained. The polymeric sulfoxide derivative thus obtained (740 mg) was dissolved in DMF (3.7 ml) at 35° C., and the reaction liquid was adjusted to 25° C. Subsequently, a Pt(R,R-dach)Cl(OTf) solution (23 mg/ml, 15 ml) produced by the method described in Reference Example 2 was added to the reaction liquid, and the mixture was stirred for 6 hours and 30 minutes. The reaction liquid was added dropwise to diisopropyl ether (270 ml), and the reaction container was washed with ethyl acetate (27 ml) into the reaction liquid. Precipitation of a yellow solid was confirmed, the reaction liquid was stirred for 15 minutes and then left to stand, and a supernatant was removed. Subsequently, diisopropyl ether (270 ml) was added to the residue, and the residue was washed by stirring. Thus, a crude form of the title compound (1.00 g) was collected by filtration. Purified water (200 ml) was added to the crude form (1.00 g), the mixture was stirred, and then the mixture was centrifuged to obtain a supernatant. A solution (100 ml) obtained by repeating membrane concentration (MWCO: 10k) and dilution was freeze-dried, and thus the title compound (691 mg) was obtained. The drug content of the compound thus obtained, in terms of Pt(R,R-dach)Cl$_2$, was 9.8% (mass fraction). Furthermore, the title compound was dissolved in purified water to a concentration of 1 mg/ml, and the particle size was measured. However, the scattering intensity was weak, and therefore, it was suggested that the title compound did not form nanoparticles.

Example 4 Production of compound of Example 4 (conjugate of polymeric sulfoxide derivative and platinum complex, obtained by introducing sulfoxide derivative (iii) into block copolymer comprising methoxy polyethylene glycol moiety having molecular weight of 12,000 and polyaspartic acid moiety having polymerization number of about 43: in General Formula (I), $R_1$=methyl group, $R_2$=trimethylene group, $R_3$=acetyl group, $R_4$=sulfoxide derivative (iii) or (iii'), $R_5$=isopropylaminocarbonylisopropylamino group or phenylalanine benzyl ester, Z=OTf, d+e+f+g+h+i+j=about 43, a=about 273)

A methoxy polyethylene glycol-polyaspartic acid block copolymer (polymerization number of aspartic acid: about 43; 3.19 g) produced by the method described in JP 3268913 B2 and methionine sulfoxide ethyl ester (743 mg) obtained in Reference Example 5 were dissolved in DMF (64.0 ml) at 35° C., and then diisopropylethylamine (2.1 ml) was added to the solution. The reaction liquid was adjusted to 25° C., and then DIPC (0.585 ml) was added thereto. After a lapse of 3 hours, phenylalanine benzyl ester hydrochloride (944 mg) and DIPC (0.52 ml) were added to the mixture, and the mixture was stirred for another one hour. DIPC (0.52 ml) was added thereto, and the mixture was stirred for one hour. Subsequently, phenylalanine benzyl ester hydrochloride (944 mg) and DIPC (1.04 ml) were added thereto, and the mixture was stirred for 19 hours. The reaction liquid was added dropwise to diisopropyl ether (640 ml), and the reaction container was washed with ethyl acetate (64 ml) into the reaction liquid. The mixture was stirred overnight at room temperature, and then a solid thus obtained was filtered and washed with diisopropyl ether (80 ml). Thus, a crude form (5.50 g) was obtained. The crude form (5.50 g) thus obtained was dissolved in a mixed liquid of acetonitrile (60 ml) and purified water (6 ml), and then the solution was passed through an ion exchange resin (manufactured by Muromachi Chemicals, Inc., MUROMAC® XSC-1114-H; 46 ml). The ion exchange resin was washed with a mixed liquid of acetonitrile (120 ml) and purified water (12 ml) into the solution, and the solution was concentrated under reduced pressure. Purified water (40 ml) was added thereto, and then the mixture was subjected to freeze-drying. Thus, a polymeric sulfoxide derivative (4.43 g) was obtained. The polymeric sulfoxide derivative (3.31 g) thus obtained was dissolved in DMF (16.6 ml) at 35° C., and the reaction liquid was adjusted to 25° C. Subsequently, a Pt(R,R-dach)Cl(OTf) solution (12.5 mg/ml, 51 ml) produced by the method described in Reference Example 2 was added to the reaction liquid, and the mixture was stirred for 24 hours. The reaction liquid was diluted about 20 times with purified water, and then a solution (60 ml) obtained by repeating membrane concentration (MWCO: 10k) and dilution was freeze-dried. Thus, the title compound (3.09 g) was obtained. The drug content of the compound thus obtained, in terms of Pt(R,R-dach)Cl$_2$, was 8.0% (mass fraction). Furthermore, the title compound was dissolved in purified water to a concentration of 1 mg/ml, and the particle size was measured. The particle size was 30 nm, and the title compound formed micelles.

Reference Example 6 Synthesis of Sulfoxide Derivative (iv)

To a mixed liquid of trifluoroacetate of the sulfoxide derivative (i) (0.5 g) synthesized in Reference Example 1, dichloromethane (3 ml), and diisopropylethylamine (0.25 ml), a dichloromethane suspension (4 ml) of 3-(4'-hydroxyphenyl)propionic acid N-hydroxysuccinimide ester (0.26 g) synthesized by referring to the method described in a non-patent literature (Biomaterials, 2010, 31, 1148-1157) was added, and the mixture was stirred at room temperature. Subsequently, diisopropylethylamine (0.5 ml) was further added to the mixture, and the mixture was stirred for 19 hours. After completion of the reaction, the reaction liquid was washed sequentially with a saturated aqueous solution of ammonium chloride and saturated brine, and anhydrous sodium sulfate was added to the organic layer. A solid was filtered, and then the filtrate was concentrated under reduced pressure. Diethyl ether was added to the residue thus obtained, and a solid was precipitated. The solid was collected by filtration and dried under reduced pressure, and thus the title compound was obtained (0.55 g). LC/MS (ESI, POS): 551 [M+H]$^+$ Example 5 Production of compound of Example 5 (conjugate of polymeric sulfoxide derivative and platinum complex, obtained by introducing sulfoxide derivative (iv) into block copolymer comprising methoxy polyethylene glycol moiety having molecular weight of 12,000 and polyglutamic acid moiety having polymerization number of about 22: in General Formula (VII), $R_{11}$=methyl group, $R_{19}$=trimethylene group, $R_{20}$=acetyl group, $R_{21}$=sulfoxide derivative (iv) or (iv'), $R_{22}$=isopropylaminocarbonylisopropylamino group, Z=OTf, k+m+n=about 22, b=about 273)

A block copolymer (0.6 g) comprising a methoxy polyethylene glycol moiety having a molecular weight of 12,000 and a polyglutamic acid moiety having a polymerization number of about 22, which had been produced by the method described in JP 4745664 B2, and the sulfoxide derivative (iv) (0.54 g) obtained in Reference Example 6 were dissolved in DMF (20 ml) at 35° C., and then DMAP (11 mg) was added thereto. The reaction liquid was adjusted to 25° C., subsequently DIPC (0.27 ml) was added thereto, and the mixture was stirred for 23.5 hours at the same temperature. Subsequently, DIPC (0.06 ml) was added thereto, and the mixture was stirred for another one hour. After completion of the reaction, the reaction liquid was slowly added to a mixed liquid of ethyl acetate (20 ml), ethanol (20 ml), and diisopropyl ether (160 ml), and the mixture was stirred at room temperature. Subsequently, the mixture was left to stand until a desired product precipitated and deposited, and a supernatant was removed. The deposit was collected by filtration and then was dried under reduced pressure, and thus a polymeric sulfoxide derivative (0.93 g) was obtained. The polymeric sulfoxide derivative (0.9 g) thus obtained was dissolved in DMF (5 ml) at 35° C., and then the solution was cooled to 25° C. Subsequently, a Pt(R,R-dach)Cl(OTf) solution (20 mg/ml, 16.7 ml) produced by the method described in Reference Example 2 was added to the solution, and the mixture was stirred for 24 hours at 25° C. After completion of the reaction, the reaction liquid was slowly added to a mixed liquid of ethyl acetate (20 ml), ethanol (20 ml), and diisopropyl ether (160 ml), and the mixture was stirred at room temperature. Subsequently, the mixture was left to stand until a desired product precipitated and deposited, and a supernatant was removed. The deposit was collected by filtration and then was dried under reduced pressure, and thereby a crude form of the title compound (1.1 g) was obtained. The crude form (1.0 g) thus obtained was purified by centrifugal ultrafiltration, VIVASPIN 20 (manufactured by Sartorius AG, MWCO: 10k), and the aqueous solution obtained after purification was freeze-dried. Thus, the title compound was obtained (0.76 g). The drug content of the compound thus obtained, in terms of Pt(R,R-dach)Cl$_2$, was 16.9% (mass fraction). Furthermore, the title compound was dissolved in purified water to a concentration of 1 mg/ml, and the particle size was measured. The particle size was 120 nm, and the title compound formed micelles.

Reference Example 7 Synthesis of Sulfoxide Derivative (vi)

Thioxanthenol sulfoxide (0.7 g) synthesized by a method described in non-patent literatures (Tetrahedron Letters, 2010, 51, 6939-6941 and J. Org. Chem., 1967, 32, 3814-3817), and N-Boc-L-phenylalanine (0.97 g) were suspended in dichloromethane (30 ml), and DMAP (74 mg) was added to the suspension. The mixture was stirred at 0° C. WSC (0.76 g) was added to the reaction liquid, and then the mixture was slowly heated to room temperature. The mixture was stirred for 2.5 hours. After completion of the reaction, the reaction liquid was washed sequentially with a saturated aqueous solution of sodium hydrogen carbonate, distilled water, and saturated brine, and anhydrous sodium sulfate was added to the organic layer. A solid was filtered, and then the filtrate was concentrated under reduced pressure. The residue thus obtained was subjected to drying under reduced pressure, and thereby a Boc-protected form of the title compound was obtained (1.45 g). The Boc-protected form (1.0 g) thus obtained was dissolved in dichloromethane (10 ml), and the solution was cooled to 0° C. Subsequently, trifluoroacetic acid (10 ml) was slowly added to the solution, and the mixture was stirred for one hour at the same temperature. After completion of the reaction, the reaction liquid was concentrated under reduced pressure, and trifluoroacetate of the title compound was obtained (0.75 g). LC/MS (ESI, POS): 475 [M+H]$^+$.

Example 6 Production of compound of Example 6 (conjugate of polymeric sulfoxide derivative and platinum complex, obtained by introducing sulfoxide derivative (vi) into block copolymer comprising methoxy polyethylene glycol moiety having molecular weight of 12,000 and polyaspartic acid moiety having polymerization number of about 43: in General Formula (I), $R_1$=methyl group, $R_2$=trimethylene group, $R_3$=acetyl group, $R_4$=sulfoxide derivative (vi) or (vi'), $R_5$=isopropylaminocarbonylisopropylamino group, Z=OTf, d+e+f+g+h+i+j=about 43, a=about 273)

A methoxy polyethylene glycol-polyaspartic acid block copolymer (polymerization number of aspartic acid: about 43; 0.82 g) produced by the method described in JP 3268913 B2 and the sulfoxide derivative (vi) (0.79 g) obtained in Reference Example 7 were dissolved in DMF (15 ml) at 35° C., and then diisopropylethylamine (0.16 ml) and DMAP (25 mg) were added to the solution. The reaction liquid was adjusted to 25° C., subsequently, DIPC (0.64 ml) was added thereto, and the mixture was stirred for 17 hours at the same temperature. Subsequently, DIPC (0.16 ml) was added thereto, and the mixture was stirred for another 2 hours. After completion of the reaction, the reaction liquid was slowly added to a mixed liquid of ethyl acetate (15 ml), ethanol (15 ml), and diisopropyl ether (120 ml), and the mixture was stirred at room temperature. Subsequently, the mixture was left to stand until a desired product precipitated and deposited, and a supernatant was removed. The deposit was collected by filtration and then was dried under reduced pressure, and thereby a polymeric sulfoxide derivative (1.27 g) was obtained. The polymeric sulfoxide derivative (1.2 g) thus obtained was dissolved in DMF (10 ml) at 35° C., and then the solution was cooled to 25° C. Subsequently, a Pt(R,R-dach)Cl(OTf) solution (20 mg/ml, 20.5 ml) produced by the method described in Reference Example 2 was added to the solution, and the mixture was stirred for 23 hours at 25° C. After completion of the reaction, the reaction liquid was slowly added to a mixed liquid of ethyl acetate (30 ml), ethanol (30 ml), and diisopropyl ether (240 ml), and the mixture was stirred at room temperature. Subsequently, the mixture was left to stand until a desired product precipitated and deposited, and a supernatant was removed. The deposit was collected by filtration and then was dried under reduced pressure, and thereby a crude form of the title compound (1.47 g) was obtained. The crude form (0.73 g) thus obtained was purified by centrifugal ultrafiltration, VIVASPIN 20 (manufactured by Sartorius AG, MWCO: 10k), and the aqueous solution obtained after purification was freeze-dried. Thus, the title compound was obtained (0.6 g). The drug content of the compound thus obtained, in terms of Pt(R,R-dach)Cl$_2$, was 13.6% (mass fraction). Furthermore, the title compound was dissolved in purified water to a concentration of 1 mg/ml, and the particle size was measured. The particle size was 126 nm, and the title compound formed micelles.

Reference Example 8 Synthesis of t-butyl (S)-(1-oxo-3-phenyl-1-thiomorpholinopropan-2-yl)carbamate N-Boc-L-phenylalanine (265 mg), thiomorpholine (104 µl), and 1-hydroxybenzotriazole monohydrate (161 mg) were suspended in a mixed solvent of ethyl acetate (5 ml) and water (2 ml), and WSC (220 mg) was added to the suspension under ice cooling. The mixture was stirred for 1.5 hours. The mixture was heated to room temperature and was further stirred for 3 hours. The reaction liquid was diluted with ethyl acetate (20 ml), and the organic layer was washed with a 5% aqueous solution of citric acid, a saturated aqueous solution of sodium hydrogen carbonate, water, and saturated brine in this order. Subsequently, the organic layer was dried over anhydrous sodium sulfate. Sodium sulfate was removed by filtration, and the solvent was distilled off under reduced pressure. The residue thus obtained was purified by silica gel column chromatography (hexane/ethyl acetate=8/2), and the title compound was obtained as a white solid (294 mg, 84%).

$^1$H-NMR (CDCl$_3$): δ7.189-7.321 (5H, m), 5.364 (1H, d), 4.804 (1H, dd), 3.839 (1H, m), 3.749 (1H, d dd), 3.518 (1H, ddd), 3.388 (1H, ddd), 2.972 (2H, d), 2.546 (1H, ddd), 2.353-2.450 (2H, m), 1.836 (1H, m), 1.420 (9H, s).

LC/MS retention time: 6.5 minutes; m/z (ESI, POS): 351 [M+H]$^+$

Reference Example 9 Synthesis of t-butyl (S)-(1-(1-oxidothiomorpholino)-1-oxo-3-phenylpropan-2-yl)carbamate To a dichloromethane (3 ml) solution of the compound obtained in Reference Example 8 (149 mg), a dichloromethane (1 ml) solution of 3-chloroperbenzoic acid (104 mg; containing about 30% of water) was added dropwise under ice cooling, and the mixture was stirred for one hour. After completion of the reaction, the reaction liquid was diluted with ethyl acetate (25 ml), and the organic layer was washed with a saturated aqueous solution of sodium hydrogen carbonate, water, and saturated brine in this order and then was dried over anhydrous sodium sulfate. Sodium sulfate was removed by filtration, and the solvent was distilled off under reduced pressure. The residue thus obtained was purified by silica gel column chromatography (ethyl acetate/methanol=8/2), and the title compound was obtained as a colorless oily material (147 mg, 94%, mixture of stereoisomers at about 1:1).

$^1$H-NMR (CDCl$_3$): δ7.172-7.327 (10H, m), 5.314 (2H, q), 4.772-4.893 (2H, m), 4.500 (1H, m), 4.406 (1H, dt), 3.902 (1H, ddd), 3.564-3.682 (5H, m), 2.921-3.096 (4H, m), 2.471-2.761 (5H, m), 2.174-2.332 (2H, m), 1.446 (9H, s), 1.412 (9H, s), 0.888 (1H, m).

LC/MS retention time: 4.9 minute; m/z (ESI, POS): 367 [M+H]$^+$

Reference Example 10 Synthesis of (S)-2-amino-1-(1-oxidothiomorpholino)-3-phenylpropan-1-one hydrochloride (Sulfoxide Derivative (vii))

To an ethanol (0.5 ml) solution of the compound obtained in Reference Example 9 (58 mg), 2 N hydrochloric acid/ethanol (2 ml) was added under ice cooling, and the mixture was stirred for 10 minutes. The mixture was heated to room temperature and was stirred for 1 hour and 10 minutes. Subsequently, 2 N hydrochloric acid/ethanol (2 ml) was added thereto, and the mixture was stirred for another 17 hours. The solvent was distilled off under reduced pressure, and the title compound was obtained as a white solid (44 mg). The title compound was used in the subsequent reaction without being purified. LC/MS retention time: 0.8 minutes; m/z (ESI, POS): 267 [M+H]$^+$ Example 7 Production of compound of Example 7 (conjugate of polymeric sulfoxide derivative and platinum complex, obtained by introducing sulfoxide derivative (vii) into block copolymer comprising methoxy polyethylene glycol moiety having molecular weight of 12,000 and polyglutamic acid moiety having polymerization number of about 22: in General Formula (VII), R$_{11}$=methyl group, R$_{19}$=trimethylene group, R$_{20}$=acetyl group, R$_{21}$=sulfoxide derivative (vii) or (vii'), R$_{22}$=isopropylaminocarbonylisopropylamino group or phenylalanine benzyl ester, Z=OTf, k+m+n=about 22, b=about 273)

A methoxy polyethylene glycol-polyglutamic acid block copolymer (polymerization number of glutamic acid: about 22; 229 mg) produced by the method described in JP 4745664 B2 and the sulfoxide derivative (vii) (41 mg) obtained in Reference Example 10 were dissolved in DMF (3.5 ml) at 35° C., and then DMAP (4.1 mg) was added to the solution. The reaction liquid was adjusted to 25° C., and then diisopropylethylamine (23 µl) and DIPC (26 µl) were added to the reaction liquid. After a lapse of 3 hours, phenylalanine benzyl ester hydrochloride (59 mg), diisopropylethylamine (35 µl), and DIPC (26 µl) were added thereto. After a lapse of 19 hours, DIPC (52 µl) was added thereto, and the mixture was stirred for another 2 hours. After completion of the reaction, the reaction liquid was slowly added to a mixed liquid of ethyl acetate (7 ml), ethanol (7 ml), and diisopropyl ether (56 ml), and the mixture was stirred at room temperature. Subsequently, the mixture was left to stand until a desired product precipitated and deposited, and a supernatant was removed. Furthermore, a mixed liquid of ethyl acetate (4 ml), ethanol (4 ml), and diisopropyl ether (32 ml) was added to the residue, the mixture was stirred at room temperature and then left to stand, and a supernatant was removed. A deposit thus obtained was further washed with ethyl acetate (2 ml), ethanol (2 ml), and diisopropyl ether (16 ml), and a solid was collected by filtration (266 mg). The crude form (255 mg) thus obtained was dissolved in acetonitrile (5 ml) and water (10 ml), subsequently an ion exchange resin (DOWEX 50 (H$^+$) manufactured by Dow Chemical Company; 3 ml) was added to the solution, and the mixture was stirred and filtered. Acetonitrile in the filtrate thus obtained was distilled off under reduced pressure, and then the residue was subjected to freeze-drying. Thus, a polymeric sulfoxide derivative (248 mg) was obtained. The polymeric sulfoxide derivative (235 mg) thus obtained was dissolved in DMF (0.5 ml) at 35° C., and then the solution was cooled to 25° C. Subsequently, a Pt(R,R-dach)Cl(OTf) solution (20 mg/ml, 1.5 ml) produced by the method described in Reference Example 2 was added to the solution, and the mixture was stirred for 23 hours. After completion of the reaction, the reaction liquid was slowly added to a mixed liquid of ethyl acetate (2 ml), ethanol (2 ml), and diisopropyl ether (16 ml), and the mixture was stirred at room temperature. The mixture was left to stand until a desired product precipitated and deposited, and a supernatant was removed. Furthermore, a mixed liquid of ethyl acetate (1 ml), ethanol (1 ml), and diisopropyl ether (8 ml) was added to the residue, the mixture was stirred at room temperature and then left to stand, and a supernatant was removed. A deposit thus obtained was further washed with a mixed liquid of ethyl acetate (0.5 ml), ethanol (0.5 ml), and diisopropyl ether (4 ml), and the deposit was collected by filtration (248 mg). A crude form (235 mg) thus obtained was dissolved in methanol (0.5 ml) and water (14.5 ml), and then the solution was purified by centrifugal ultrafiltration using VIVASPIN 20 (manufactured by Sartorius AG, MWCO: 10k) and freeze-dried. Thus, the title compound (220 mg) was obtained. The drug content of the compound thus obtained, in terms of Pt(R,R-dach)$Cl_2$, was 8.8% (mass fraction). Furthermore, the title compound was dissolved in purified water to a concentration of 1 mg/ml, and the particle size was measured. The particle size was 28 nm, and the title compound formed micelles.

Example 8 Production of compound of Example 8 (conjugate of polymeric sulfoxide derivative and platinum complex, obtained by introducing sulfoxide derivative (viii) into block copolymer comprising methoxy polyethylene glycol moiety having molecular weight of 12,000 and polyglutamic acid moiety having polymerization number of about 22: in General Formula (VII), $R_{11}$=methyl group, $R_{19}$=trimethylene group, $R_{20}$=acetyl group, $R_{21}$=sulfoxide derivative (viii) or (viii'), $R_{22}$=isopropylaminocarbonylisopropylamino group or phenylalanine benzyl ester, k+m+n=about 22, b=about 273)

A methoxy polyethylene glycol-polyglutamic acid block copolymer (polymerization number of glutamic acid: about 22; 500 mg) synthesized by the method described in JP 4745664 B2; 4-(phenylsulfinyl)phenol (113 mg) synthesized by the method described in J. Org. Chem., 2011, 76, 4635-4644; and phenylalanine benzyl ester hydrochloride (65 mg) were dissolved in DMF (12.5 ml) at 35° C., and then the reaction liquid was adjusted to 25° C. DMAP (14 mg) and diisopropylethylamine (0.042 ml) were added to the reaction liquid, and then DIPC (0.213 ml) was added thereto. After a lapse of 19 hours, DIPC (0.213 ml) was added thereto, and the mixture was stirred for 3 hours. After completion of the reaction, the reaction liquid was slowly added to a mixed liquid of ethyl acetate (37.5 ml) and diisopropyl ether (150 ml), and the mixture was stirred at room temperature. The mixture was left to stand until a desired product precipitated and deposited, and the supernatant was removed. The deposit thus obtained was further washed with ethyl acetate/ diisopropyl ether (1/4 (v/v); 50 ml), and a crude form was collected by filtration. The crude form thus obtained was dissolved in a 50% aqueous solution of acetonitrile (12 ml) that had been cooled to 0° C., and then an ion exchange resin (DOWEX 50 ($H^+$) manufactured by Dow Chemical Company; 3 ml) was added to the solution. The mixture was shaken for 45 minutes. After the ion exchange resin was separated by filtration, the filtrate was concentrated and freeze-dried, and thereby a polymeric sulfoxide derivative (586 mg) was obtained. The polymeric sulfoxide derivative (500 mg) thus obtained was dissolved in DMF (5 ml) at 35° C., and then the solution was cooled to 25° C. Subsequently, a Pt(R,R-dach)Cl(OTf) solution (20 mg/ml, 3.4 ml) produced by the method described in Reference Example 2 was added to the solution, and the mixture was stirred for 24 hours. After completion of the reaction, the reaction liquid was slowly added to a mixed liquid of ethyl acetate (25 ml) and diisopropyl ether (100 ml), and the mixture was stirred at room temperature. Subsequently, the mixture was left to stand until a desired product precipitated and deposited, and the deposit was collected by filtration. A crude form thus obtained was dissolved in methanol/water (4/9 (v/v); 13 ml), and then the solution was subjected to centrifugal ultrafiltration using VIVASPIN 20 (manufactured by Sartorius, MWCO: 10k) to thereby remove low molecular weight compounds. The solution obtained after purification was subjected to freeze-drying, and thus the title compound (434 mg) was obtained. The drug content of the compound thus obtained, in terms of Pt(R,R-dach)$Cl_2$, was 9.3% (mass fraction). Furthermore, the title compound was dissolved in purified water to a concentration of 1 mg/ml, and the particle size was measured. The particle size was 28 nm, and the title compound formed micelles.

Reference Example 11 Synthesis of 2-(4-phenylsulfinyl)phenoxy)ethylamine hydrochloride (Sulfoxide Derivative (ix))

4-(Phenylsulfinyl)phenol (200 mg) synthesized by the method described in J. Org. Chem., 2011, 76, 4635-4644, potassium carbonate (190 mg), and potassium iodide (228 mg) were suspended in DMF (1.8 ml), and 2-bromo-N-Boc-ethylamine (308 mg) was added to the suspension. The mixture was stirred at 50° C. After a lapse of 25 hours, 2-bromo-N-Boc-ethylamine (103 mg) and potassium carbonate (63 mg) were added to the mixture, and the mixture was stirred for another 25 hours. After completion of the reaction, distilled water and dichloromethane were added thereto, and an aqueous layer was extracted three times with dichloromethane. An organic layer thus obtained was washed with a 1 N aqueous solution of sodium hydroxide and saturated brine, and then the organic layer was dried by adding anhydrous sodium sulfate thereto. The organic layer was filtered and then concentrated, and a crude form was obtained. The crude form thus obtained was purified by silica gel column chromatography (hexane:ethyl acetate=4: 1→1:2 (v'v)), and N-Boc-2-(4-(phenylsulfinyl)phenoxy) ethylamine (300 mg) was obtained. N-Boc-2-(4-(phenylsulfinyl)phenoxy)ethylamine (273 mg) thus obtained was dissolved in ethanol (1.9 ml), and a 2 N hydrochloric acid/ethanol solution (5.7 ml) was added to the solution at 0° C. Subsequently, the mixture was stirred for 24 hours. After completion of the reaction, the reaction liquid was concentrated, and thus the title compound (216 mg) was obtained.

$^1$H-NMR ($D_2O$): δ7.55-7.75 (7H, m), 7.17 (2H, d, J=8.8 Hz), 4.35 (2H, t, J=4.9 Hz), 3.46 (2H, t, J=4.9 Hz).

Example 9 Production of compound of Example 9 (conjugate of polymeric sulfoxide derivative and platinum complex, obtained by introducing sulfoxide derivative (ix) into block copolymer comprising methoxy polyethylene glycol moiety having molecular weight of 12,000 and polyaspartic acid moiety having polymerization number of about 43: in General Formula (I), $R_1$=methyl group, $R_2$=trimethylene group, $R_3$=acetyl group, $R_4$=sulfoxide derivative (ix) or (ix'), $R_5$=isopropylaminocarbonylisopropylamino group or phenylalanine benzyl ester, d+e+f+g+h+i+j=about 43, a=about 273)

A methoxy polyethylene glycol-polyaspartic acid block copolymer (polymerization number of aspartic acid: about 43; 80 mg) synthesized by the method described in JP 3268913 B2, 2-(4-(phenylsulfinyl)phenoxy)ethylamine hydrochloride (40 mg) described in Reference Example 11, and phenylalanine benzyl ester hydrochloride (18 mg) were dissolved in DMF (2 ml) at 35° C., and then the reaction liquid was adjusted to 20° C. 1-Hydroxybenzotriazole monohydrate (34 mg) and diisopropylethylamine (0.039 ml) were added to the reaction liquid, and then DIPC (0.058 ml) was added thereto. The mixture was stirred for 25 hours. After completion of the reaction, the reaction liquid was slowly added to a mixed liquid of ethanol (8 ml) and diisopropyl ether (32 ml), and the mixture was stirred at room temperature. Subsequently, the mixture was left to stand until a desired product precipitated and deposited, and a supernatant was removed. The deposit thus obtained was further washed with ethanol/diisopropyl ether (1/4 (v/v); 10 ml), and a crude form was collected by filtration. The crude form thus obtained was dissolved in a 50% aqueous solution of acetonitrile (6 ml) that had been cooled to 0° C., and then an ion exchange resin (DOWEX 50 (H$^+$) manufactured by Dow Chemical Company; 1 ml) was added to the solution. The mixture was shaken for one hour. After the ion exchange resin was separated by filtration, the filtrate was concentrated and subjected to freeze-drying, and thus a polymeric sulfoxide derivative (111 mg) was obtained. The polymeric sulfoxide derivative (88 mg) thus obtained was dissolved in DMF (0.9 ml) at 35° C., and then the solution was cooled to 25° C. Subsequently, a Pt(R,R-dach)Cl(OTf) solution (20 mg/ml, 0.8 ml) produced by the method described in Reference Example 2 was added to the solution, and the mixture was stirred for 24 hours. After completion of the reaction, the reaction liquid was slowly added to a mixed liquid of ethyl acetate (5 ml) and diisopropyl ether (20 ml), and the mixture was stirred at room temperature. Subsequently, the mixture was left to stand until a desired product precipitated and deposited, and the deposit was collected by filtration. A crude form thus obtained was dissolved in methanol/water (2/7 (v/v); 9 ml), and then the solution was subjected to centrifugal ultrafiltration using VIVASPIN 20 (manufactured by Sartorius AG, MWCO: 10k) to thereby remove low molecular weight compounds. The solution obtained after purification was freeze-dried, and thereby the title compound (85 mg) was obtained. The drug content of the compound thus obtained, in terms of Pt(R,R-dach)Cl$_2$, was 11.3% (mass fraction). Furthermore, the title compound was dissolved in purified water to a concentration of 1 mg/ml, and the particle size was measured. The particle size was 28 nm, and the title compound formed micelles.

Example 10 Production of compound of Example 10 (conjugate of polymeric sulfoxide derivative and platinum complex, obtained by introducing sulfoxide derivative (viii) into block copolymer comprising methoxy polyethylene glycol moiety having molecular weight of 2,000 and polyglutamic acid moiety having polymerization number of about 8: in General Formula (VII), $R_{11}$=methyl group, $R_{19}$=trimethylene group, $R_{20}$=acetyl group, $R_{21}$=sulfoxide derivative (viii) or (viii'), $R_{22}$=isopropylaminocarbonylisopropylamino group or phenylalanine benzyl ester, k+m+n=about 8, b=about 46)

A methoxy polyethylene glycol-polyglutamic acid block copolymer (polymerization number of glutamic acid: about 8; 600 mg) synthesized by referring to the method described in JP 4745664 B2; 4-(phenylsulfinyl)phenol (203 mg) synthesized by the method described in J. Org. Chem., 2011, 76, 4635-4644; and phenylalanine benzyl ester hydrochloride (181 mg) were dissolved in DMF (18 ml) at 35° C., and then the reaction liquid was adjusted to 25° C. DMAP (28 mg) and diisopropylethylamine (0.118 ml) were added to the reaction liquid, and then DIPC (0.477 ml) was added thereto. After a lapse of 15.5 hours, DIPC (0.477 ml) was added thereto, and the mixture was further stirred for 5 hours. After completion of the reaction, the reaction liquid was slowly added to a mixed liquid of ethyl acetate (18 ml) and diisopropyl ether (162 ml), and the mixture was stirred at room temperature. The mixture was left to stand until a product precipitated and deposited, and the supernatant was removed. The precipitate thus obtained was further washed with two times with diisopropyl ether (180 ml) and was dried under reduced pressure, and thereby a polymeric sulfoxide derivative (953 mg) was obtained. The polymeric sulfoxide derivative (953 mg) thus obtained was dissolved in dimethylformamide (10.9 ml) at 35° C., and then the solution was cooled to 25° C. Subsequently, a Pt(R,R-dach)Cl(OTf) solution (20 mg/ml, 12.1 ml) produced by the method described in Reference Example 2 was added to the solution, and the mixture was stirred for 23 hours. After completion of the reaction, the reaction liquid was slowly added to a mixed liquid of diisopropyl ether (230 ml), and the mixture was stirred at room temperature. The mixture was left to stand until a desired product precipitated, and the supernatant was removed. A precipitate thus obtained was further washed two times with diisopropyl ether (230 ml) and was dried under reduced pressure. A crude form thus obtained was dissolved in water (60 ml), and then a solid was precipitated using a centrifuge. The supernatant was subjected to centrifugal ultrafiltration using VIVASPIN 20 (manufactured by Sartorius AG, MWCO: 3k), and low molecular weight compounds were removed. An aqueous solution of maltose (40 mg/ml, 67.5 ml) and an aqueous solution of Macrogol 4000 (20 mg/ml, 67.5 ml) were added to the solution obtained after purification, and the mixture was freeze-dried. Thereby, a composition including the title compound (4.62 g) was obtained. The drug content in terms of Pt(R,R-dach)Cl$_2$ in the composition was 1.2% (mass fraction). Furthermore, the title compound was dissolved in purified water to a concentration of 1 mg/ml, and the particle size was measured. The particle size was 18 nm, and the title compound formed micelles.

Example 11 Production of compound of Example 11 (conjugate of polymeric sulfoxide derivative and platinum complex, obtained by introducing sulfoxide derivative (x) into block copolymer comprising methoxy polyethylene glycol moiety having molecular weight of 12,000 and polyaspartic acid having polymerization number of about 43: in General Formula (I), $R_1$=methyl group, $R_2$=trimethylene group, $R_3$=acetyl group, $R_4$=sulfoxide derivative (x) or (x'), $R_5$ isopropylaminocarbonylisopropylamino group, d+e+f+g+h+i+j=about 43, a=about 273)

A block copolymer (800 mg) comprising a methoxy polyethylene glycol moiety and a moiety having a structure in which aspartic acid-alanine (4-phenyl-1-butanol) ester was bonded to a side chain of a polyaspartic acid having a polymerization number of about 43, which had been produced by the method described in WO 2010/131675, and thioxanthenol sulfoxide (152 mg) synthesized by a method described in non-patent literatures (Tetrahedron Letters, 2010, 51, 6939-6941 and J. Org. Chem., 1967, 32, 3814-3817) were dissolved in DMF (10 ml) at 35° C., and then DMAP (13 mg) was added to the solution. The reaction liquid was adjusted to 25° C., and then DIPC (0.227 ml) was added thereto. After a lapse of 23 hours, DIPC (0.070 ml) was added thereto, and the mixture was stirred for another one hour. After completion of the reaction, the reaction liquid was slowly added to diisopropyl ether (160 ml), and the mixture was stirred at room temperature. Subsequently, the mixture was left to stand until a desired product precipitated and deposited, and a supernatant was removed. The deposit thus produced was collected by filtration and then was subjected to drying under reduced pressure. Thus, a polymeric sulfoxide derivative (784 mg) was obtained. The polymeric sulfoxide derivative (750 mg) thus obtained was dissolved in DMF (5 ml) at 35° C., and then the solution was cooled to 25° C. Subsequently, a Pt(R,R-dach)Cl(OTf) solution (20 mg/ml, 9.3 ml) produced by the method described in Reference Example 2 was added to the solution, and the mixture was stirred for 24 hours. After completion of the reaction, the reaction liquid was slowly added to a mixed liquid of ethyl acetate (15 ml), ethanol (15 ml), and diisopropyl ether (120 ml), and the mixture was stirred at room temperature. Subsequently, the mixture was left to stand until a desired product precipitated and deposited, and the deposit was collected by filtration. A crude form thus obtained was dissolved in methanol/water (1/8 (v/v); 36 ml), and then the solution was subjected to centrifugal ultrafiltration using VIVASPIN TURBO15 (manufactured by Sartorius AG, MWCO: 10k) to thereby remove low molecular weight compounds. The solution obtained after purification was freeze-dried, and thereby the title compound (716 mg) was obtained. The drug content of the compound thus obtained, in terms of Pt(R,R-dach)Cl$_2$, was 10.5% (mass fraction). Furthermore, the title compound was dissolved in purified water to a concentration of 1 mg/ml, and the particle size was measured. The particle size was 80 nm, and the title compound formed micelles.

Example 12 Production of compound of Example 12 (conjugate of polymeric sulfoxide derivative and platinum complex, obtained by introducing sulfoxide derivative (x) into block copolymer comprising methoxy polyethylene glycol moiety having molecular weight of 2,000 and polyaspartic acid moiety having polymerization number of about 12: in General Formula (I), $R_1$=methyl group, $R_2$=trimethylene group, $R_3$=acetyl group, $R_4$=sulfoxide derivative (x) or (x'), $R_5$=isopropylaminocarbonylisopropylamino group, d+e+f+g+h+i+j=about 12, a=about 46) A block copolymer (700 mg) comprising a methoxy polyethylene glycol moiety and a moiety having a structure in which aspartic acid-alanine (4-phenyl-1-butanol) ester was bonded to a side chain of a polyaspartic acid having a polymerization number of about 12, which had been produced by the method described in WO 2010/131675, and thioxanthenol sulfoxide (183 mg) synthesized by a method described in non-patent literatures (Tetrahedron Letters, 2010, 51, 6939-6941 and J. Org. Chem., 1967, 32, 3814-3817) were dissolved in DMF (9 ml) at 35° C., and then DMAP (16 mg) was added to the solution. The reaction liquid was adjusted to 25° C., and then DIPC (0.344 ml) was added to the reaction liquid. After a lapse of 24 hours, DIPC (0.084 ml) was added thereto, and the mixture was stirred for another one hour. After completion of the reaction, the mixture was slowly added to diisopropyl ether (300 ml), and the mixture was stirred at room temperature. Subsequently, the mixture was left to stand until a desired product precipitated and deposited, and a supernatant was removed. The deposit thus produced was collected by filtration and then was subjected to drying under reduced pressure. Thus, a polymeric sulfoxide derivative (641 mg) was obtained. The polymeric sulfoxide derivative (620 mg) thus obtained was dissolved in DMF (5 ml) at 35° C., and then the solution was cooled to 25° C. Subsequently, a Pt(R,R-dach)Cl(OTf) solution (20 mg/ml, 7 ml) produced by the method described in Reference Example 2 was added to the solution, and the mixture was stirred for 24 hours. After completion of the reaction, the mixture was slowly added to diisopropyl ether (130 ml), and the mixture was stirred at room temperature. Subsequently, the mixture was left to stand until a desired product precipitated and deposited, and the deposit was collected by filtration. A crude form thus obtained was dissolved in acetonitrile/water (1/19 (v/v); 36 ml), and then the solution was subjected to centrifugal ultrafiltration using VIVASPIN TURBO15 (manufactured by Sartorius AG, MWCO: 10k) to thereby remove low molecular weight compounds. To an aqueous solution thus obtained, trehalose dihydrate (2.4 g) and Macrogol 4000 (1.2 g) were added, and the mixture was freeze-dried. Thereby, a mixture (3.8 g) of the title compound, trehalose, and Macrogol 4000 was obtained. The drug content in terms of Pt(R,R-dach)Cl$_2$ in the composition was 0.85% (mass fraction).

Test Example 1 Surface Charge and Particle Size of Example Compounds

Each of the Example compounds was dissolved in purified water to a concentration of 1 mg/ml, and the zeta potential (surface charge) and the particle size were measured. The results are presented in Table 1.

TABLE 1

| Compound | $R_4$ | Surface charge (zeta potential) mV | Particle size nm |
|---|---|---|---|
| Example 1 compound | (i) or (i') | +16.2 | 85 |
| Example 2 compound | (ii) or (ii') | +28.7 | 60 |
| Example 3 compound | (iii) or (iii') | +2.0 | — |
| Example 4 compound | (iii) or (iii') | +11.6 | 30 |
| Example 5 compound | (iv) or (iv') | +22.1 | 120 |
| Example 6 compound | (vi) or (vi') | +28.5 | 126 |
| Example 7 compound | (vii) or (vii') | +14.0 | 28 |
| Example 8 compound | (viii) or (viii') | +9.4 | 50 |
| Example 9 compound | (ix) or (ix') | +1.2 | 103 |
| Example 10 compound | (viii) or (viii') | +14.8 | 18 |
| Example 11 compound | (x) or (x') | +21.8 | 80 |

It was confirmed that the various tested Example compounds all exhibited positive (plus) surface charge (zeta potential). Furthermore, from the results of the particle size measurement, it was suggested that all the Example compounds, except for Example 3 compound, formed nano-sized micelles.

Test Example 2 Concentration/Time Dependency of Proliferation Inhibitory Action to DAN-G Cells <Cells>

Human pancreatic cancer cell line, DAN-G, was purchased from Asta Medica GmbH, and the cells were proliferated and subcultured in a recommended medium described in the pamphlet.

<Proliferation Inhibition Test>

For DAN-G cells that had been cultured and proliferated on a 10 cm dish for cell culture, the culture fluid was removed, and the cells were washed once with 5 ml of PBS (phosphate buffered physiological saline). Subsequently, 1 ml of 0.25% trypsin/0.05% EDTA (ethylenediaminetetraacetic acid)/PBS was added to the cells, and the mixture was left to stand for 5 minutes at 37° C. After it was confirmed that the cells had been detached from the dish, 9 ml of medium was added to the dish to disperse the cells, the dispersion was transferred into a 15 ml tube (Corning, Inc.), and the dispersion was centrifuged for 5 minutes at 1,000 rpm. A supernatant was removed, subsequently 10 ml of fresh medium was added to the tube, and the cells were suspended. A portion of the cells was stained with Trypan Blue, and the viable cell count was measured using a hemocytometer. The suspended cells were diluted with medium to a concentration of $2.6 \times 10^4$ cells/ml, and the cells were inoculated onto five sheets of 96 well plate (Plates A, B, C, D, and E) at a volume of 190 μl/well ($5 \times 10^3$ cells/well).

The cells were cultured overnight, and then 10 μl/well of the Example 1 compound dissolved in a 5% glucose solution was added to the cells at a concentration (drug content concentration in terms of DACH-platin) of 0, 0.024, 0.098, 0.39, 1.56, 6.25, 25, or 100 μM. The cells were then cultured under the conditions of 37° C. and 5% $CO_2$. Three replica wells were provided for each drug concentration.

A test was performed under five different conditions by changing the drug addition time.

For Plate A, the medium was removed after 2 hours from the addition of drug, the cells were washed three times with 200 μl of medium, fresh medium that did not contain a drug was added to the plate at a volume of 200 μl/well, and the cells were further cultured for 70 hours under the conditions of 37° C. and 5% $CO_2$.

For Plate B, the medium was removed after 6 hours from the addition of drug, the cells were washed three times with 200 μl of medium, fresh medium that did not contain a drug was added to the plate at a volume of 200 μl/well, and the cells were further cultured for 66 hours under the conditions of 37° C. and 5% $CO_2$.

For Plate C, the medium was removed after 24 hours from the addition of drug, the cells were washed three times with 200 μl of medium, fresh medium that did not contain a drug was added to the plate at a volume of 200 μl/well, and the cells were further cultured for 48 hours under the condition of 37° C. and 5% $CO_2$.

For Plate D, the medium was removed after 48 hours from the addition of drug, the cells were washed three times with 200 μl of medium, fresh medium that did not contain a drug was added to the plate at a volume of 200 μl/well, and the cells were further cultured for 24 hours under the conditions of 370 and 5% $CO_2$.

For Plate E, the medium was removed after 72 hours from the addition of drug, the cells were washed three times with 200 μl of medium, fresh medium that did not contain a drug was added to the plate at a volume of 200 μl/well, and a staining process as described below was immediately performed.

For Plates A, B, C, D, and E that had been cultured for 72 hours as described above, the medium was removed, subsequently methanol was added to the plates, and the cells were thereby immobilized on the plates. After methanol was removed, a 0.05% Methylene Blue solution was added to the plate, and the cells were stained for 30 minutes. Methylene Blue was removed, any excess stain solution was washed with water, subsequently 3% hydrochloric acid was added to the plate at a volume of 200 μl/well, and thus Methylene Blue was extracted. The plates were left to stand for 2 hours or longer, and the absorbance at 660 nm was measured using a microplate reader (BENCHMARK PLUS, manufactured by Bio-Rad Laboratories, Inc.). Regarding the measured values, the average value of three replicas of a well for each drug concentration was taken. The proliferation inhibition ratio GI(x) % at a drug concentration x was calculated by the following formula from the absorbance values thus measured.

$$GI(x)\% = (1-(A_x-B)/(A_0-B)) \times 100$$

Ax represents the absorbance of a well having a drug concentration x; A0 represents the absorbance of a solvent control well to which no drug was added; and B represents the absorbance of a blank well that did not contain any cells or drug.

A similar test was performed also for Example 2 compound and 1-OHP. The $IC_{50}$ values (drug concentrations at which the GI % value becomes 50%) of the various drugs are presented in Table 2.

TABLE 2

| $IC_{50}$ (μM) | 2 hour | 6 hours | 24 hours | 48 hours | 72 hours | $IC_{50}$ (6 hours)/ $IC_{50}$ (72 hours) |
|---|---|---|---|---|---|---|
| Example 1 compound | 90.9 | 58.9 | 39.7 | 31.2 | 36.1 | 1.6 |
| Example 2 compound | 48.9 | 35.6 | 16.2 | 13.0 | 13.6 | 2.6 |
| 1-OHP | 44.1 | 9.0 | 1.8 | 0.9 | 0.9 | 10.0 |

The $IC_{50}$ (6 hours)/$IC_{50}$ (72 hours) value of 1-OHP was 10.0, which implied that as the drug exposure time was prolonged, the $IC_{50}$ value was significantly reduced. Meanwhile, the $IC_{50}$ (6 hours)/$IC_{50}$ (72 hours) values of the Example 1 compound and the Example 2 compound were 1.6 and 2.6, respectively. Thus, even if the drug exposure time was prolonged, the $IC_{50}$ values did not change significantly.

From the results of Test Examples 1 and 2 described above, it was suggested that since a conjugate of a platinum complex, in which the polymeric sulfoxide derivative is coordinate-bonded to platinum, is positively charged, the conjugate does not require a long drug exposure time, the conjugate is rapidly taken into cells, and thereby the conjugate exhibits efficacy.

Test Example 3 Antitumor Effect on Human Gastric Cancer 4-1ST-Transplanted Mouse <Animal and Transplanted Tumor>

Human gastric cancer 4-1ST was subcultured and maintained subcutaneously in BALB/cA-nu/nu mice (hereinafter, nude mice). Human gastric cancer 4-1ST was purchased from Central Institute for Experimental Animals.

<Antitumor Test 1>

Human gastric cancer 4-1ST was collected from the subcutaneous sites of nude mice, and the tumors were finely cut into blocks each measuring about 3 mm on one side. The tumor blocks thus obtained were transplanted subcutaneously into the dorsal side of nude mice using a trocar. On the $18^{th}$ day after transplantation, when the average tumor volume reached about 100 to 200 $mm^3$, various drugs were intravenously administered through the caudal vein. The dosage and administration of the various drugs administered were as follows: the Example 1 compound was dissolved in 5% glucose injection liquid, and the solution was administered once at doses of 75 mg/kg and 150 mg/kg. The Example 2 compound was dissolved in 5% glucose injection liquid, and the solution was administered once at doses of 75 mg/kg and 150 mg/kg. As control drugs, 1-OHP was administered once at a dose of 20 mg/kg, and cisplatin was administered once at a dose of 10 mg/kg. Regarding the amounts of administration of 1-OHP and cisplatin, and the high amounts of administration of the various Example compounds, the maximum tolerable dose (MTD dose) was employed in all cases.

After the administration of the various drugs, the major axes (L) and the minor axes (W) of the tumors were measured over time using calipers, and the tumor volumes (L×W×W×0.5) were calculated. The test was carried out using four animals per group in all cases for a non-administered group and various drug-administered groups. For a period starting from the initiation of administration to the $20^{th}$ day after administration, the relative tumor volume (T/C (%)) of each of the drug-administered groups was calculated by the following formula, based on the relative tumor volume of the non-administered group as 100, as an index of the antitumor effect. The T/C (%) values of the various drug-administered groups are presented in Table 3.

T/C (%)=Relative tumor volume of administered group/relative tumor volume of non-administered group×100     Formula:

TABLE 3

| Compound | Amount of administration mg/kg | T/C (%) on days after each administration | | | | | | |
|---|---|---|---|---|---|---|---|---|
| | | 0 | 3 | 6 | 9 | 13 | 16 | 20 |
| Non-administered group | | 100 | 100 | 100 | 100 | 100 | 100 | 100 |
| Example 1 compound | 75 | 100 | 78 | 40 | 35 | 35 | 38 | 40 |
| | 150 | 100 | 54 | 18 | 11 | 5 | 5 | 6 |
| Example 2 compound | 75 | 100 | 90 | 68 | 65 | 63 | 59 | 69 |
| | 150 | 100 | 72 | 38 | 28 | 29 | 22 | 26 |
| l-OHP | 20 | 100 | 96 | 53 | 46 | 46 | 51 | 50 |
| Cisplatin | 10 | 100 | 91 | 49 | 32 | 31 | 35 | 36 |

<Antitumor Test 2>

Human gastric cancer 4-1ST was collected from subcutaneous sites of nude mice, and the tumors were finely cut into blocks each measuring about 3 mm on one side. The tumor blocks thus obtained were transplanted subcutaneously into the dorsal side of nude mice using a trocar. On the 18$^{th}$ day after transplantation, when the average tumor volume reached about 100 to 200 mm$^3$, various drugs were intravenously administered through the caudal vein. The dosage and administration of the various drugs administered were as follows: the Example 3 compound was dissolved in 5% glucose injection liquid, and the solution was administered once at doses of 75 mg/kg and 150 mg/kg. The Example 4 compound was dissolved in 5% glucose injection liquid, and the solution was administered once at doses of 100 mg/kg and 200 mg/kg. As a control drug, 1-OHP was administered once at a dose of 18 mg/kg. Regarding the high amounts of administration of 1-OHP and Example 4 compound, the maximum tolerable dose (MTD dose) was employed in both cases. Regarding Example 3 compound, the dose was less than or equal to the MTD dose; however, the dissolution limit of the compound was administered. After the administration of the various drugs, the major axes (L) and the minor axes (W) of the tumors were measured over time using calipers, and the tumor volumes (L×W×W×0.5) were calculated. The test was carried out using four animals per group in all cases for a non-administered group and various drug-administered groups. For a period starting from the initiation of administration to the 21$^{st}$ day after administration, the T/C (%) values of the various drug-administered groups are presented in Table 4.

TABLE 4

| Compound | Amount of administration mg/kg | T/C (%) on days after each administration | | | | | | |
|---|---|---|---|---|---|---|---|---|
| | | 0 | 3 | 7 | 10 | 14 | 17 | 21 |
| Non-administered group | 0 | 100 | 100 | 100 | 100 | 100 | 100 | 100 |
| Example 3 compound | 75 | 100 | 98 | 80 | 81 | 86 | 95 | 97 |
| | 150 | 100 | 96 | 65 | 65 | 66 | 70 | 73 |
| Example 4 compound | 100 | 100 | 106 | 69 | 63 | 67 | 81 | 75 |
| | 200 | 100 | 86 | 45 | 45 | 53 | 72 | 80 |
| l-OHP | 18 | 100 | 100 | 65 | 58 | 57 | 61 | 60 |

From the results described above, the Example 1 compound and the Example 2 compound exhibited superior antitumor effect compared to 1-OHP. Particularly, the Example 1 compound maintained an antitumor effect higher than or equal to that of 1-OHP even at low doses, and noticeable regression of tumors was observed at high doses. The Example 3 compound and the Example 4 compound exhibited an antitumor effect to the same extent as that of 1-OHP.

<Antitumor Test 3>

Human gastric cancer 4-1ST was collected from subcutaneous sites of nude mice, and the tumors were finely cut into blocks each measuring about 3 mm on one side. The tumor blocks thus obtained were transplanted subcutaneously into the dorsal side of nude mice using a trocar. On the 17$^{th}$ day after transplantation, when the average tumor volume reached about 100 to 200 mm$^3$, various drugs were intravenously administered through the caudal vein. The dosage and administration of the various drugs administered were as follows: the Example 6 compound was dissolved in 5% glucose injection liquid, and the solution was administered once at doses of 12.5 mg/kg and 25 mg/kg. The Example 11 compound was dissolved in 5% glucose injection liquid, and the solution was administered once at doses of 5 mg/kg and 10 mg/kg. As a control drug, 1-OHP or cisplatin (CDDP) was administered once at a dose of 18 mg/kg or 10 mg/kg. Regarding the high amounts of administration of the administered compounds, the maximum tolerable dose (MTD dose) was employed in all cases. After the administration of the various drugs, the major axes (L) and the minor axes (W) of the tumors were measured over time using calipers, and the tumor volumes (L×W×W×0.5) were calculated. The test was carried out using four animals per group in all cases for a non-administered group and various drug-administered groups. For a period starting from the initiation of administration to the 21$^{st}$ day after administration, the T/C (%) values of the various drug-administered groups are presented in Table 5.

After the administration, the body weights of the mice were measured over time. For a period starting from the initiation of administration to the 21$^{st}$ day after administration, the changes in the relative body weights based on the body weight on the day of initiation of administration as 1 are presented in Table 6.

TABLE 5

| Compound | Amount of administration mg/kg | T/C (%) on days after each administration | | | | | | |
|---|---|---|---|---|---|---|---|---|
| | | 0 | 4 | 7 | 11 | 14 | 18 | 21 |
| Non-administered group | | 100 | 100 | 100 | 100 | 100 | 100 | 100 |
| Example 6 compound | 12.5 | 100 | 81 | 71 | 60 | 51 | 46 | 47 |
| | 25 | 100 | 50 | 30 | 23 | 22 | 25 | 25 |
| Example 11 compound | 5 | 100 | 83 | 58 | 55 | 52 | 50 | 52 |
| | 10 | 100 | 72 | 31 | 26 | 27 | 21 | 21 |
| l-OHP | 18 | 100 | 84 | 52 | 50 | 50 | 60 | 57 |
| Cisplatin | 10 | 100 | 77 | 43 | 32 | 36 | 37 | 42 |

TABLE 6

| Compound | Amount of administration mg/kg | Relative body weight on days after administration | | | | | | |
|---|---|---|---|---|---|---|---|---|
| | | 0 | 4 | 7 | 11 | 14 | 18 | 21 |
| Non-administered group | | 1.00 | 0.99 | 0.97 | 0.96 | 1.00 | 1.03 | 1.00 |
| Example 6 compound | 12.5 | 1.00 | 0.93 | 0.95 | 0.98 | 1.02 | 1.03 | 1.00 |
| | 25 | 1.00 | 0.83 | 0.87 | 0.96 | 1.02 | 1.05 | 1.00 |
| Example 11 compound | 5 | 1.00 | 0.98 | 1.00 | 0.98 | 1.02 | 1.03 | 1.04 |
| | 10 | 1.00 | 0.90 | 0.90 | 0.95 | 1.03 | 1.05 | 1.01 |
| l-OHP | 18 | 1.00 | 0.78 | 0.83 | 0.93 | 1.03 | 1.09 | 1.05 |
| Cisplatin | 10 | 1.00 | 0.80 | 0.79 | 0.85 | 0.92 | 0.99 | 0.98 |

From the results described above, the Example 6 compound and the Example 11 compound exhibited an obviously superior antitumor effect compared to l-OHP, and an antitumor effect equal to or higher than that of cisplatin, at the MTD doses. Also at the 50% MTD doses, the Example compounds maintained an antitumor effect equal to or higher than that of l-OHP. Meanwhile, the body weight reduction on the $4^{th}$ day after administration in the cases of the Example 6 compound and the Example 11 compound was negligible compared to l-OHP and cisplatin, and it was found that side effects were reduced.

From the results of the antitumor tests described above, it was found that polymer conjugates of platinum(II) complexes, in which a sulfoxide derivative has been introduced into a side-chain carboxyl group in a block copolymer comprising a polyethylene glycol structural moiety and a polyaspartic acid moiety or a polyglutamic acid moiety, and the sulfoxide group is coordinate-bonded, exhibit antitumor effects superior to that of l-OHP.

The invention claimed is:

1. A polymer conjugate of a platinum(II) complex, the polymer conjugate comprising:
   a block copolymer having a polyethylene glycol structural moiety and a polyaspartic acid moiety;
   a sulfoxide derivative introduced into a side-chain carboxyl group of the block copolymer; and
   a platinum(II) complex coordinate-bonded to a sulfoxide group of the sulfoxide derivative;
   wherein the polymer conjugate is represented by the following General Formula (I):

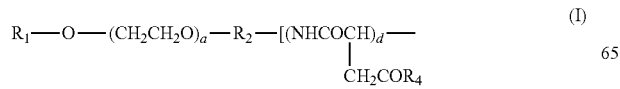

(I)

-continued $$\text{---(NHCOCH}_2\text{CH)}_e\text{---(NHCOCH)}_f\text{---(NHCOCH}_2\text{CH)}_g\text{---}$$
with side chains $COR_4$, $CH_2COR_5$, $COR_5$ $$\text{---(NHCOCH)}_h\text{---(NHCOCH}_2\text{CH}_2)_i\text{---(NCOCH)}_j\text{---NHR}_3$$
with side chains $CH_2CO_2H$, $CO_2H$, $COCH_2$ wherein $R_1$ represents a methyl group; $R_2$ represents a trimethylene group; $R_3$ represents an acetyl group; $R_4$ represents a substituent selected from the group consisting of substituents represented by the following Formula (V):

(V)

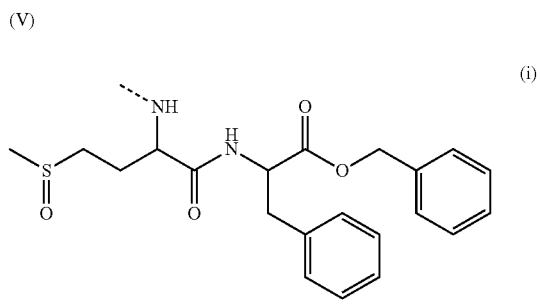

(i)

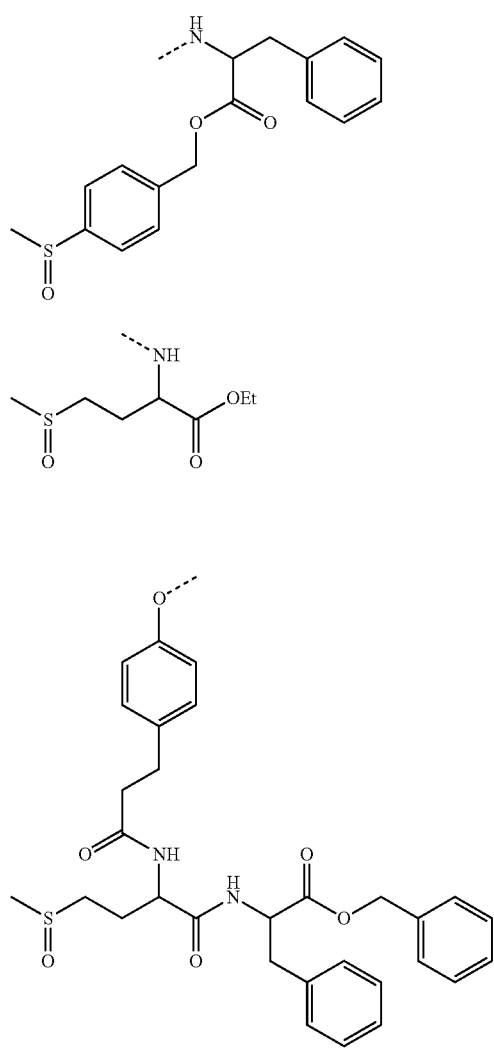
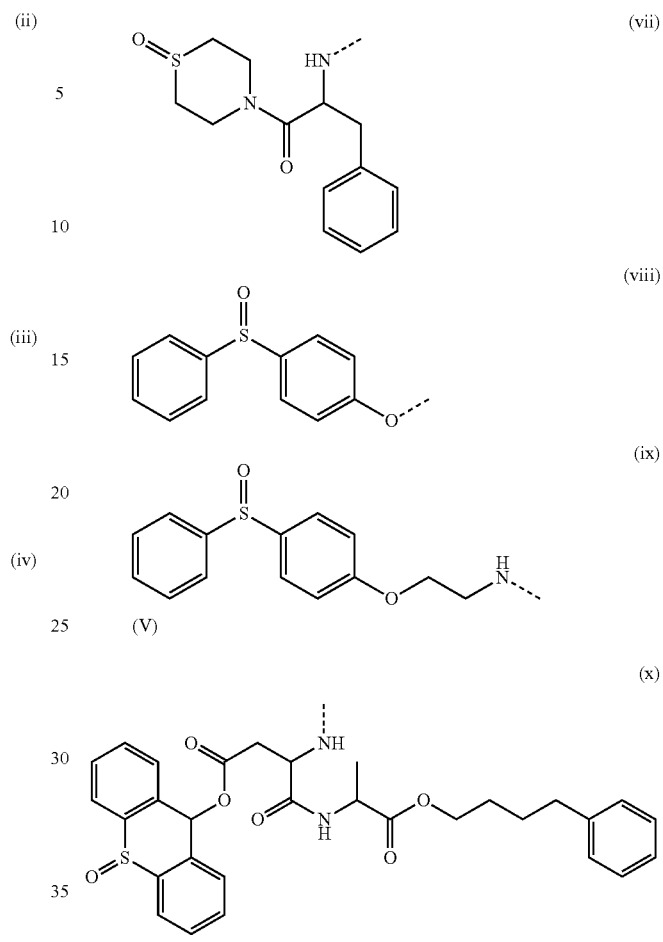
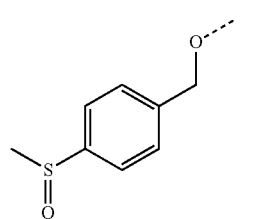
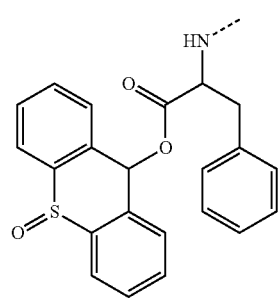
or a substituent selected from the group of substituents represented by the following Formula (VI):
(VI)
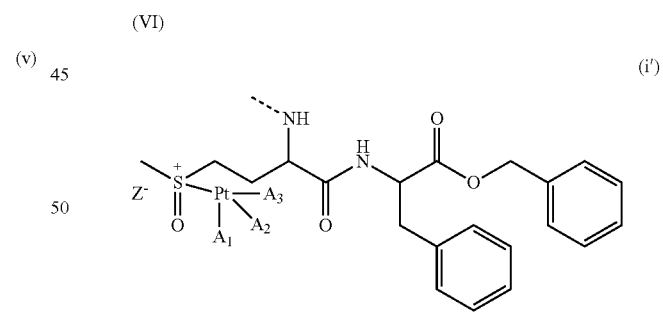
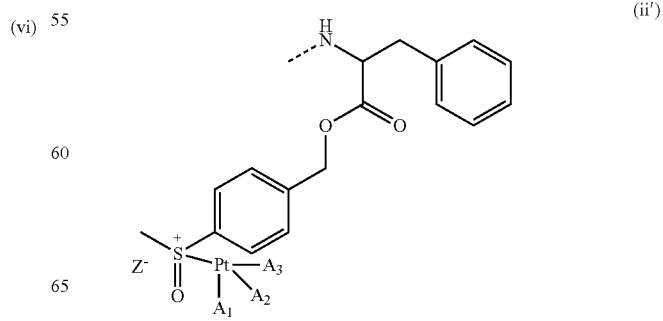

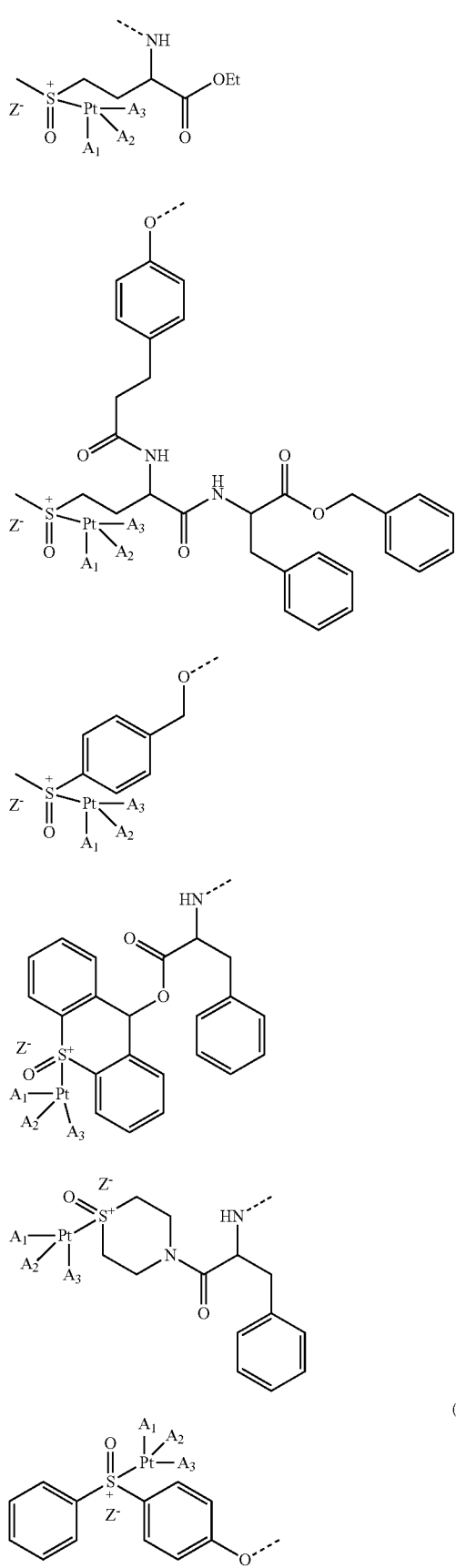

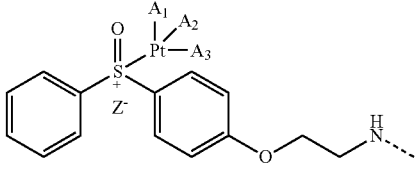

(VI)

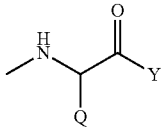

(x')

wherein $A_1, A_2, A_3$ each represent a ligand of the platinum complex and $Z^-$ represents a counter anion;

at least one of $R_4$ represents a substituent coordinate-bonded to the platinum complex represented by Formula (VI);

$R_5$ represents a substituent represented by the following General Formula (IV) obtained by eliminating H from an α-amino group of an α-amino acid derivative:

(IV)

with a benzyl group as Q, or $-NR_9CONHR_{10}$; and $R_9$ and $R_{10}$ both represent a cyclohexyl group or an isopropyl group;

a represents an integer from 10 to 2,000; d, e, f, g, h, i, and j each represent an integer from 0 to 100; d+e represents an integer from 1 to 100; d+e+f+g+h+i+j represents an integer from 4 to 100; and the order of bonding of the various constituent units of polyaspartic acid is random.

2. The polymer conjugate of a platinum(II) complex according to claim 1, wherein the ligands $A_1$ and $A_2$ of the platinum complex both represent ammonia or a primary, secondary or tertiary amine, or are bonded together to form a non-cyclic or cyclic diamine optionally having a substituent; and $A_3$ represents a halogen atom, a water molecule, an amine optionally having a substituent, a heteroaryl compound, or a sulfoxide compound.

3. The polymer conjugate of a platinum(II) complex according to claim 2, wherein the ligands $A_1$ and $A_2$ of the platinum complex both represent ammonia or a ligand selected from the group of ligands represented by the following Formula (XIII):

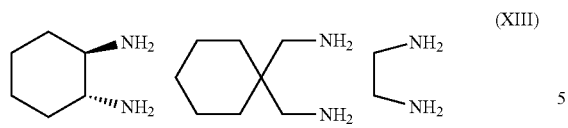 (XIII)
and $A_3$ represents a chlorine atom.
4. A medicine comprising the polymer conjugate of a platinum(II) complex according to claim 1 as an active ingredient.
5. An antitumor agent comprising the polymer conjugate of a platinum(II) complex according to claim 1 as an active ingredient.
* * * * *